(12) United States Patent
Nadeson et al.

(10) Patent No.: US 8,268,821 B2
(45) Date of Patent: Sep. 18, 2012

(54) METHODS AND COMPOSITIONS

(75) Inventors: Raymond Nadeson, Lethbridge (AU);
Adam Paul Tucker, Hawthorn (AU);
Colin Goodchild, Malvern (AU)

(73) Assignee: Relevare Aust. Pty Ltd (AU)

(*) Notice: Subject to any disclaimer, the term of this patent is extended or adjusted under 35 U.S.C. 154(b) by 0 days.

(21) Appl. No.: 12/958,210

(22) Filed: Dec. 1, 2010

(65) Prior Publication Data

US 2011/0092482 A1 Apr. 21, 2011

Related U.S. Application Data

(63) Continuation of application No. 10/574,438, filed as application No. PCT/AU2004/001772 on Dec. 16, 2004.

(30) Foreign Application Priority Data

Dec. 16, 2003 (AU) .............................. 2003906981

(51) Int. Cl.
*A61K 31/445* (2006.01)
*A61K 31/44* (2006.01)
*A61K 31/535* (2006.01)
*A61K 31/454* (2006.01)

(52) U.S. Cl. .................. 514/235.5; 514/231.2; 514/352; 514/282; 514/291; 514/295; 514/326; 514/329; 514/330; 514/353; 514/348; 514/349; 514/18.5

(58) Field of Classification Search ............... 514/235.5, 514/282, 291, 295, 326, 329, 330, 353, 231.2, 514/348, 349, 18.4, 352
See application file for complete search history.

(56) References Cited

U.S. PATENT DOCUMENTS

| | | | |
|---|---|---|---|
| 4,778,799 A | 10/1988 | Tibes et al. | 514/277 |
| 5,521,178 A | 5/1996 | Nickel et al. | 514/231.2 |
| 6,022,875 A | 2/2000 | Zimmer et al. | 514/252 |
| 6,221,395 B1 | 4/2001 | Maggi et al. | 424/475 |
| 6,610,324 B2 | 8/2003 | Stoll | 424/464 |
| 6,916,486 B2 | 7/2005 | Klose et al. | 424/448 |
| 2003/0082214 A1 | 5/2003 | Williams et al. | 424/400 |
| 2004/0092531 A1* | 5/2004 | Chizh et al. | 514/255.05 |
| 2008/0039463 A1 | 2/2008 | Nadeson et al. | |

FOREIGN PATENT DOCUMENTS

| | | |
|---|---|---|
| CA | 2102072 C | 5/1994 |
| CA | 2314746 A1 | 2/2001 |
| CN | 1399550 A | 2/2003 |

(Continued)

OTHER PUBLICATIONS

Kleihues et al. (WHO classification of tumors of the nervous system, Journal of Neuropathology and experimental Neurology, 2002, vol. 61 (3), pp. 215-225).*

(Continued)

*Primary Examiner* — Savitha Rao

(57) ABSTRACT

The present invention relates generally to the field of pain management, and in particular, the management of neuropathic or inflammatory pain including a neuropathic or inflammatory component of nociceptive pain. More particularly, the present invention provides methods and compositions which treat, alleviate, prevent, diminish or otherwise ameliorate the symptoms of neuropathic or inflammatory pain. The present invention further contemplates combination therapy involved in the treatment of pain in association with the treatment of a particular disease condition or pathology. The present invention further also provides sustained and slow release formulations, tamper-proof deliver systems and stents, catheters and other mechanical devices coated with formulations which permit sustained or slow release of active ingredients involved in pain management.

6 Claims, 3 Drawing Sheets

FOREIGN PATENT DOCUMENTS

| | | |
|---|---|---|
| EP | 207 193 A2 | 1/1987 |
| EP | 595 311 A1 | 5/1994 |
| EP | 795 324 A2 | 9/1997 |
| JP | 6-211663 | 8/1994 |
| JP | 9-316005 | 12/1997 |
| JP | 2003-530308 | 10/2003 |
| WO | WO 01/08682 A2 | 2/2001 |

OTHER PUBLICATIONS

Chi et al., "A Study on in vitro Drug Release Pattern of Multi-layered Controlled-Release Matrix Tablets Containing Tramadol Hydrochloride," Journal of Shenyang Pharmaceutical University 18(2): 88-90, Mar. 2001.

Cleary, "Cancer Pain Management," Cancer Control, 7 (2): 120-131, 2000.

Devulder et al., "Central Pain: an overview," Acta Neurologica Belgica, 102 (3): 97-103, 2002.

Friedel et al., "Flupirtine. A review of it's pharmacological properties, and therapeutic efficacy in pain states," Drugs 45(4): 548-569, 1993.

Gribkoff, "The therapeutic potential of neuronal KCNQ channel modulators," Expert Opinion on Therapeutic Targets 7(6): 737-748, Dec. 2003.

Grond et al., "Assessment and treatment of neuropathic cancer pain following WHO guidelines," Pain, 79: 15-20, 1999.

Herrmann et al., "On the adverse reactions and efficacy of long-term treatment with flupirtine: preliminary results of an ongoing twelve-month study with 200 patients suffering from chronic states in arthrosis or arthritis," Postgraduate Medical Journal 63: 87-103, 1987.

International Search Report for PCT/AU2004/001772, mailed Mar. 1, 2005, 5 pages.

Li et al., "Recent Pharmacology Progress in Flupirtine, A new Analgesic Agent," Chinese Journal of New Drugs 11(10): 759-763, Oct. 1, 2002 (+English Translation).

Nickel, "Pharmacological activity of flupirtine in combination with morphine," Regional Anesthesia & Pain Medicine 18 (4): p. 4, 1993.

Perovic et al., "Flupirtine Partially Prevents Neuronal Injury Induced by Prion Protein Fragment and Lead Acetate," Neurodegeneration, 4 (4): 369-374, 1995.

RX-s.net, URL=http://rx-s.net/weblog/more/acetaminophen-codeine/, download date Nov. 3, 2010.

Schuster et al., "Flupirtine: A review of its neuroprotective and behavioural properties," CNS Drug Reviews 4(2): 149-164, 1998.

Yu Jin-gui et al., "Enhanced Analgesia Effect of NMDA Receptor Antagonist on Opium," Foreign Medical Sciences—Anesthesiology and Resucitation 20(2): 85-87, 1990 (English translation only).

Gary J. Bennett et al., "A peripheral mononeuropathy in rat that produces disorders of pain sensation like those seen in man," Pain, 1988, vol. 33: pp. 87-107.

David A. Brown, et al., "Neural KCNQ (Kv7) channels," British Journal of Pharmacology, 2009, vol. 156; pp. 1185-1195.

Huei-Sheng Vincent Chen et al., "The chemical biology of clinically tolerated NMDA receptor antagonists," Journal of Neurochemistry, 2006, vol. 97: pp. 1611-1626.

Wayne E. Childers Jr et al., "N0Methyl-D-Aspartate Antagonists and Neuropathic Pain: The Search for Relief," J. Med. Chem., 2007, vol. 50: pp. 2557-2562.

Anton J.M. de Craen et al., "Analgesic efficacy and safety of paracetamol-codeine combinations versus paracetamol alone: a systematic review," BMJ, 1996, vol. 313: pp. 321-325.

Raymond A. Dionne, "Additive Analgesic Effects of Oxycodone and Ibuprofen in the Oral Surgery Model," J. Oral Maxillofac Surg., 1999, vol. 57: pp. 673-678.

Robert H. Dworkin et al., "Pharmacologic management of neuropathic pain: Evidence-based recommendations," Pain, 2007, vol. 132: pp. 237-251.

Bradley S. Galer et al., "Development and preliminary validation of a pain measure specific to neuropathic pain: The Neuropathic Pain Scale," Neurology, 1997, vol. 48; pp. 332-338.

Colin S. Goodchild et al., "Combination Therapy with Flupirtine and Opioid: Open-Label Case Series in the Treatment of Neuropathic Pain Associated with Cancer," Pain Medicine, 2008, vol. 9, No. 7: pp. 939-949.

Valentine K. Gribkoff, "The therapeutic potential of neuronal KCNQ channel modulators," Expert Opin. Ther. Targets, 2003, vol. 7, No. 6: pp. 737-748.

Guideline Central, "Guideline: Pharmacologic management of neuropathic pain: Evidence-based recommendations," accessed on Feb. 9, 2010, 19 pages, URL: http://www.guidelinecentral.com/CustomContentRetrieve.aspx?ID=1826487&A=Searc.

P. Hlavica et al., "Investigation on the Pharmacokinetics and Biotransformations of the Analgesic Flupirtine in Humans," Arzneimittelferschun, 1985, vol. 35: pp. 67-74 English Translation.

Regina Jakob et al., "Innuence of flupirtine on a G-protein coupled inwardly rectifying potassoum current in hippocampal neurones," British Journal of Pharmacology, 1997, vol. 122: pp. 1333-1338.

Sun Ho Kim et al., "An experimental model for peripheral neuropathy produced by segmental spinal nerve ligation in the rat," Pain, 1992, vol. 50: pp. 355-363.

J. Kornhuber et al., "Flupirtine shows functional NMDA receptor antagonism by enhancing Mg2+ block via activation of voltage independent potassium channels," J. Neural Transm, 1999, vol. 106: pp. 857-867.

Maria Martire, et al., "M Channels Containing KCNQ2 Subunits Modeulate Norepinephorine, Aspartate, and GABA Release from Hippocampal Nerve Terminals," The Journal of Neuroscience, Jan. 21, 2004, vol. 24, No. 3; pp. 592-597.

F. Gilbert McMahon, et al., "Clinical experience with flupirtine in the U.S.," Postgraduate Medical Journal, 1987, vol. 63: pp. 81-85.

Francesco Miceli, et al., "Molecular pharmacology and therapeutic potential of neuronal Kv7-modulating drugs," Current Opinion in Pharmacology, 2008, vol. 8; pp. 65-74.

Gordon Munro, et al., "Kv7 (KCNQ) Channel Modulators and Neuropathic Pain," J. Med. Chem., 2007, vol. 50; pp. 2576-2582.

Kimball Nill, "Glossary of Biotechnology Terms," 3rd Edition, CRC Press, 2002: p. 13.

N. N. Osborne et al., "Protection of Rabbit Retina From Ischemic Injury by Flupirtine," Investigative Opthalmology & Visual Science, Feb. 1996, vol. 37, No. 2: pp. 274-280.

C. G. Parsons, et al., "Comparative Patch-clamp Studies with Freshly Dissociated Rat Hippocampal and Sriatal Neurons on the NMDA Receptor Antagonistic Effects of Amantadine and Memantine," European Journal of Neuroscience, 1996, V. 8; pp. 446-454.

Gayle M. Passmore, et al., "KCNQ/M Currents in Sensory Neurons: Significance for Pain Therapy," The Journal of Neuroscience, Aug. 6, 2003, vol. 23, No. 18; pp. 7227-7236.

Navil F. Sethna et al., "Analgestic and Cognitive Effects of Intravenous Ketamine-Alfentanil Combinations Versus Either Drug Alone After Intradermal Capsaicin in Normal Subiects," Anesth Anald, 1998, vol. 86: pp. 1250-1256.

Megumi Shimoyama et al., "Gabapentin enhances the antinociceptive effects of spinal morphine in the rat tail-flick test," Pain, 1997, vol. 72: pp. 375-382.

Hong-Sheng Wang, et al., "KCNQ2 and KCNQ3 Potassium Channels Subunits: Molecular Correlates of the M-Channel," Science, 1998, vol. 282; pp. 1890-1893.

Yong-Jin Wu, et al., "(S)-N-[1-(3-Morpholin-4-ylphenyl)ethyl]-3-phenylacrylamide: An Orally Bioavailable KCNQ2 Opener with Significant Activity in a Cortical Spreading Depression Model of Migraine," J. Med. Chem., 2003, vol. 46; pp. 3197-3200.

Heike Wulff,et al., "Voltage-gated Potassium Channels as Therapeutic Drug Targets," Nat Reev Drug Discov., Dec. 8, 2008, vol. 8, No. 12; pp. 982-1001.

\* cited by examiner

METHODS AND COMPOSITIONS

CROSS-REFERENCES TO RELATED APPLICATIONS

This application is a continuation of U.S. patent application Ser. No. 10/574,438, filed Jun. 25, 2007, now pending, which application is a U.S. national phase of International Application No. PCT/AU2004/001772, filed Dec. 16, 2004, which application claims priority to Australian Application No. 2003906981, filed Dec. 16, 2003, which applications are incorporated herein by reference in their entirety.

BACKGROUND OF THE INVENTION

1. Field of the Invention

The present invention relates generally to the field of pain management, and in particular, the management of neuropathic or inflammatory pain including a neuropathic or inflammatory component of nociceptive pain. More particularly, the present invention provides methods and compositions which treat, alleviate, prevent, diminish or otherwise ameliorate the symptoms of neuropathic or inflammatory pain. The present invention further contemplates combination therapy involved in the treatment of pain in association with the treatment of a particular disease condition or pathology. The present invention further also provides sustained and slow release formulations, tamper-proof deliver systems and stents, catheters and other mechanical devices coated with formulations which permit sustained or slow release of active ingredients involved in pain management.

2. Description of the Prior Art

Bibliographical details of references provided in the subject specification are listed at the end of the specification.

Reference to any prior art in this specification is not, and should not be taken as, an acknowledgment or any form of suggestion that this prior art forms part of the common general knowledge in any country.

Pain is an unpleasant sensory and emotional experience associated with actual or potential tissue damage or described in such terms. In considering approaches to treatment of pain, it is important to understand the distinction between acute and persistent or chronic pain. Acute pain occurs as a result of tissue injury, and is mediated by chemical, mechanical or thermal stimulation of pain receptors known as nociceptors. In contrast to acute pain, chronic or persistent pain in itself constitutes a disease which serves no protective biological function. Chronic pain is unrelenting and can persist for years and frequently cannot be associated with a single injury. Chronic pain predominantly constitutes chronic inflammatory pain (e.g. arthritis) or "neuropathic pain" which can be defined as pain initiated or caused by a primary lesion or dysfunction within the nervous system (Mersky and Bogduk *Classifications of Chronic Pain, 2$^{nd}$ edn. Seattle IASP Press:* 394, 1994, De Andres and Garcia-Ribas Pain Practice 3:1-7, 2003). Neuropathic pain is associated with a variety of disease states and present in the clinic with a wide range of symptoms. (Woolf and Mannion *Lancet* 353:1959-64, 1999) It does not require specific pain receptor stimulation although such stimulation can add to the intensity of the pain sensation (Baron *Clin J Pan* 16 (suppl2):S12-S20, 2003).

Neuropathic pain is often reported as having a lancinating or continuous burning character and is frequently associated with the appearance of abnormal sensory signs such as allodynia and hyperalgesia. Alloydnia is defined as pain resulting from a stimulus that does not normally elicit a painful response, and hyperalgesia is characterized by an increased pain response to normally non-painful stimuli. Some disorders characterized by neuropathic pain include monoradiculopathies, trigeminal neuralgia, postherpetic neuralgia, phantom limb pain, complex regional pain syndromes, back pain and the various peripheral neuropathies. Neuropathic pain may also be associated with diabetes, radio- or chemotherapy and infections such as HIV. Neuropathic pain may also result as a side effect of drug treatment or abuse.

For clinical purposes, nociceptive pain can be classified as somatic or visceral. Somatic pain results from prolonged activation of nociceptive receptors in somatic tissues such as a bone, joint, muscle or skin. Visceral pain, on the other hand manifests from activation of nociceptive receptors by pathological mechanisms such as mechanical injury, x-ray irradiation and toxic agents.

Neuropathic pain can be characterized by the following clinical features (Teng and Mekhail *Pain Practice* 3:8-12, 2003, Rajbhandari et al *Pain,* 83:627-629, 1999, Melzack et al *Ann NY Acad Sci,* 933: 157-174, 2001):

1. There is the presence of an abnormal, unpleasant sensation (dysesthesia) that frequently has a burning or electrical quality with an occasional paroxysmal, brief, shooting, or stabbing quality.

2. Although the onset of most neuropathic pain is within days after the precipitating injury, there is no absolute temporal relationship to the originating neural trauma such that it can begin weeks, months, or even years later.

3. Pain may be felt in a region of sensory deficit.

4. Non-noxious stimuli may be painful (allodynia).

5. Noxious stimuli may produce greater than normal response (hyperalgesia).

6. There may be an increase in the intensity of pain with repeated stimuli and the pain may persist after the removal of stimuli.

There are no analgesic agents specific for one type of pain component over another and neuropathic and nociceptive pains often respond differently to various analgesics.

Accordingly, although there are numerous available therapies for acute pain caused by stimulation of the nociceptors, especially treatment with opioid and non-steroidal anti-inflammatory drugs (NSAIDs), neuropathic pain is an area of largely unmet therapeutic need. Due to the distinct pathophysiochemical mechanisms and clinical manifestations associated with neuropathic pain relative to pain caused as a result of nociceptor stimulation or acute pain, agents useful in the treatment of pain caused as a result of nociceptor stimulation or acute pain have reduced effectiveness in neuropathic pain treatment. In particular, the effectiveness of opioids in the treatment of neuropathic pain is diminished relative to their use in the treatment of pain caused as a result of nociceptor stimulation or acute pain, and drug dose response curves for treatment of neuropathic pain are shifted to the right of those for treatment of pain caused as a result of nociceptor stimulation or acute pain (Teng and Mekhail, 2003 supra, De Andres and Garcia-Ribas, 2003 supra, Stute et al *J. Pain Symptom Management* 25:1123-1131, 2003).

Due to the diminished effects of opioids in subjects suffering from neuropathic pain, the use of opioids is often frequent and sustained. This over use is often associated with addiction, the development of tolerance and an increase in the number and severity of side effects associated with opioid use. These side effects include euphoric effects, emetic effects, spastic constipation and increased smooth muscle tone.

The conventional pharmacological mainstays of clinical management of neuropathic pain are the tricyclic anti-depressants and certain anti-convulsants, but even these achieve a reduction in pain of less than 50% in greater than 50% of patients treated. These agents are also associated with significant side effect profiles.

There is a pressing need for improved regimes for the treatment of neuropathic and inflammatory pain as well as improved regimes for treating disease conditions which have a neuropathic or inflammatory pain component.

SUMMARY OF THE INVENTION

Throughout the specification and the claims which follow, unless the context requires otherwise, the word "comprise", and variations such as "comprises" and "comprising" will be understood to imply the inclusion of a stated integer or step or group of integers or steps but not the exclusion of any other integer or step or group of integers or steps.

The present invention provides methods and compositions which treat, alleviate, prevent, diminish or otherwise ameliorate the symptoms associated with neuropathic and/or inflammatory pain in a subject. Reference to "neuropathic pain" or "inflammatory pain" includes the neuropathic or inflammatory component of nociceptive pain. In particular, the present invention contemplates a method for inducing an analgesic response to neuropathic or inflammatory pain in a mammal comprising administering to the mammal an amount of flupirtine or a pharmaceutically acceptable salt, derivative, homolog or analog thereof effective to reduce the level of or otherwise ameliorate the sensation of pain. In a related aspect, the compositions and methods of the present invention do not induce overt sedation and/or cause reduced side effects associated with agents used in the treatment of pain.

The present invention also provides a method of inducing an analgesic response in a mammal suffering neuropathic or inflammatory pain by administering to the mammal one of an analgesic agent or flupirtine or a pharmaceutically acceptable salt, derivative, homolog or analog thereof concurrently, separately or sequentially with respect to the other of an analgesic agent or flupirtine or a pharmaceutically acceptable salt, derivative, homolog or analog thereof, in an amount effective to reduce the level of or otherwise ameliorate the sensation of pain. Preferably, the flupirtine or a pharmaceutically acceptable salt derivate, homolog or analog thereof is administered in an amount effective to reduce at least one adverse side effect of the analgesic agent. Such an effective amount is considered a synergistic effective amount. Preferably, the method does not induce overt sedation such as caused by the analgesic agent. Preferably, the analgesic agent is an opioid, such as but not limited to fentanyl, oxycodone, codeine, dihydrocodeine, dihydrocodeinone enol acetate, morphine, desomorphine, apomorphine, diamorphine, pethidine, methadone, dextropropoxyphene, pentazocine, dextromoramide, oxymorphone, hydromorphone, dihydromorphine, noscapine, papverine, papveretum, alfentanil, buprenorphine and tramadol and pharmaceutically acceptable salts, derivatives, homologs or analogs thereof as well as opioid agonists.

Another embodiment the present invention relates to the use of flupirtine or a pharmaceutically acceptable salt, derivative, homolog or analog thereof in the manufacture of a medicament for inducing an analgesic response in the treatment of neuropathic or inflammatory pain. Preferably, the analgesia is induced without overt sedation and preferably the pain is neuropathic pain.

In a further embodiment, the present invention relates to the use of an analgesic agent and flupirtine or a pharmaceutically acceptable salt, derivative, homolog or analog thereof, in the manufacture of one or more separate or combined medicaments for inducing analgesia in response to inflammatory or neuropathic pain. Preferably, the analgesia is induced without overt sedation and preferably the pain is neuropathic pain. In a preferred embodiment the analgesic agent is an opioid and preferably the opioid is selected from one or more of the opioids listed above or a pharmaceutically acceptable salt, derivatives, homologs or analogs thereof.

In a further embodiment, the present invention contemplates combination therapy such as in the treatment of cancer, inflammation, a neurological condition or a chronic disease or condition or other pathology wherein the treatment of the disease, condition or pathology is conducted in association with pain management using flupirtine or a pharmaceutically acceptable salt, derivative, homolog or analog thereof or optionally an opioid or another analgesic compound.

In a still further embodiment of the present invention, there is provided a delivery system for inducing analgesia in response to neuropathic or inflammatory pain in a mammal comprising an analgesic agent and flupirtine or a pharmaceutically acceptable salt, derivative, homolog or analog thereof. In a preferred embodiment the analgesic agent is an opioid and preferred the opioid is selected from one or more of the opioids listed above or pharmaceutically acceptable salts, derivatives, homologs or analogs thereof. The delivery system may, for example, be in the form of a sustained release or slow release formulation, or a tamper proof formulation, or a pharmaceutical formulation or coated onto a stent, catheter or other mechanical device designed for use in a medical procedure.

The compounds according to the present invention may be administered, inter alia, orally, transmucosally, rectally including via suppository, subcutaneously, intravenously, intramuscularly, intraperitoneally, intragastrically, intranasally, intrathecally, transdermally or intestinally. In particularly preferred forms of the present invention, the compounds are orally or transdermally administered.

The present invention further provides a method of treatment of a condition such as cancer, back pain, inflammation or a neurological condition which has a neuropathic or inflammatory pain component, the treatment comprising the administration of flupirtine and optionally an opioid or a pharmaceutically acceptable salts, derivatives, homologs or analogs thereof.

Preferably, the flupirtine or pharmaceutically acceptable salt, derivative, homolog or analog thereof is administered at a dose of between about 0.5 mg/kg and about 20 mg/kg, at intervals of between about 1 hour and about 50 hours, when administered either alone or in combination with an analgesic agent. Preferably, the intervals are between about 12 hours and about 24 hours.

In a particularly preferred embodiment of the present invention the mammal is a human.

A further aspect of the subject invention provides a system for the controlled release of flupirtine or a pharmaceutically acceptable salt, derivative, homolog or analog thereof and optionally an opioid, alone or together with another analgesic or active agent, wherein the system comprises:

(a) a deposit-core comprising an effective amount of an active substance and having defined geometric form, and (b) a support-platform applied to the deposit-core, wherein the deposit-core contains at least one active substance, and at least one member selected from the group consisting of:

(i) a polymeric material which swells on contact with water or aqueous liquids and a gellable polymeric material wherein the ratio of the swellable polymeric material to the gellable polymeric material is in the range 1:9 to 9:1, and (ii) a single polymeric material having both swelling and gelling properties, and wherein the support-platform is an elastic support applied to the deposit-core so that it partially covers the surface of the deposit-core and follows changes due to hydration of the deposit-core and is slowly soluble and/or slowly gellable in aqueous fluids.

The present invention further provides an agent for inducing an analgesic response in a mammal, the agent comprising flupirtine or a pharmaceutically acceptable salt, derivative, homolog or analog thereof and optionally an analgesic compound such as an opioid and optionally an active compound for treating a condition, disease or pathology. In one particular example, the present invention contemplates a treatment protocol for cancer, the protocol comprising the administration of a anti-cancer agent and/or radiation therapy in combination with flupirtine and optionally an opioid or a pharmaceutically acceptable salt, derivative, homolog or analog thereof.

DETAILED DESCRIPTION OF THE PREFERRED EMBODIMENTS

Figure 1:
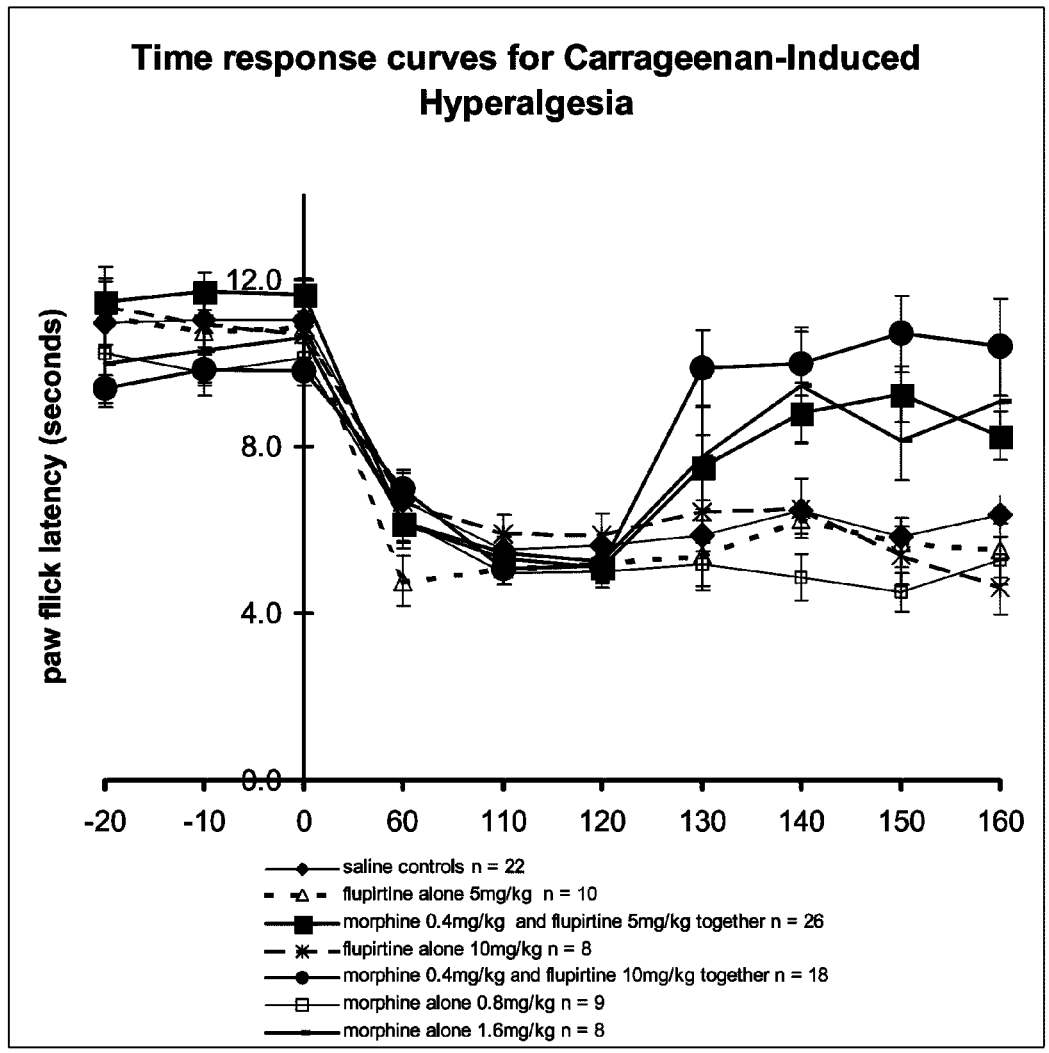
FIG. 1 is a graphical representation of time response curves for carrageenan-induced hyperalgesia in male Wistar rats, where paw flick latency (seconds) is plotted against time (minutes) for saline controls (diamonds), flupirtine at 5 mg/kg (squares), flupirtine at 10 mg/kg (stars), morphine at 0.8 mg/kg (vertical bars), morphine at 1.6 mg/kg (horizontal bars), the combination of flupirtine at 5 mg/kg with morphine at 0.4 mg/kg (squares) and the combination of flupirtine at 10 mg/kg with morphine at 0.4 mg/kg (circles).

Before describing the present invention in detail, it is to be understood that unless otherwise indicated, the subject invention is not limited to specific formulations of components, manufacturing methods, dosage regimes, or the like, as such may vary. It is also to be understood that the terminology used herein is for the purpose of describing particular embodiments only, and is not intended to be limiting.

The singular forms "a", "an" and "the" include plural aspects unless the context clearly dictates otherwise. Thus, for example, reference to "an opioid" includes a single opioid, as well as two or more opioids; reference to "an analgesic agent" includes a single agent, as well as two or more agents.

In describing and claiming the present invention, the following terminology is used in accordance with the definitions set forth below.

The terms "compound", "agent", "active agent", "chemical agent", "pharmacologically active agent", "medicament", "active" and "drug" are used interchangeably herein to refer to a chemical compound that induces a desired pharmacological and/or physiological effect. The terms also encompass pharmaceutically acceptable and pharmacologically active ingredients of those active agents specifically mentioned herein including but not limited to salts, esters, amides, prodrugs, active metabolites, analogs and the like. When the terms "compound", "agent", "active agent", "chemical agent" "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc.

Reference to a "compound", "agent", "active agent", "chemical agent" "pharmacologically active agent", "medicament", "active" and "drug" includes combinations of two or more actives such as two or more opioids. A "combination" also includes multi-part compositions such as a two-part composition where the agents are provided separately and given or dispensed separately or admixed together prior to dispensation.

For example, a multi-part pharmaceutical pack may have two or more active agents maintained separately.

The terms "effective amount" and "therapeutically effective amount" of an agent as used herein mean a sufficient amount of the agent (e.g. flupirtine and/or an opioid) to provide the desired therapeutic or physiological effect or outcome. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms of the condition being treated, elimination of symptoms and/or underlying cause, prevention of the occurrence of symptoms of the condition and/or their underlying cause and improvement or remediation or amelioration of damage following a condition.

"Treating" a subject may involve prevention of a condition or other adverse physiological event in a susceptible individual as well as treatment of a clinically symptomatic individual by ameliorating the symptoms of the condition.

A "subject" as used herein refers to an animal, preferably a mammal and more preferably human who can benefit from the pharmaceutical formulations and methods of the present invention. There is no limitation on the type of animal that could benefit from the presently described pharmaceutical formulations and methods. A subject regardless of whether a human or non-human animal may be referred to as an individual, patient, animal, host or recipient. The compounds and methods of the present invention have applications in human medicine, veterinary medicine as well as in general, domestic or wild animal husbandry. The compositions also have industrial applications.

As indicated above, the preferred animals are humans or other primates such as orangutans, gorillas, marmosets, livestock animals, laboratory test animals, companion animals or captive wild animals, as well as avian species.

Examples of laboratory test animals include mice, rats, rabbits, simian animals, guinea pigs and hamsters. Rabbits, rodent and simian animals provide a convenient test system or animal model. Livestock animals include sheep, cows, pigs, goats, horses and donkeys.

The present invention provides a method of an inducing analgesic response to neuropathic or inflammatory pain in a mammal. In this context the term "mammal" is intended to encompass both humans and other mammals such as laboratory test animals.

Throughout this specification, the term "neuropathic pain" is to be understood to mean pain initiated or caused by a primary lesion or dysfunction within the nervous system. Examples of categories of neuropathic pain that may be treated by the methods of the present invention include mono-radiculopathies, trigeminal neuralgia, postherpetic neuralgia, phantom limb pain, complex regional pain syndromes, back pain, neuropathic pain associated with AIDS and infection with the human immunodeficiency virus and the various peripheral neuropathies, including, but not limited to drug-induced and diabetic neuropathies.

The term "inflammatory pain" is intended to describe the subset of acute and chronic pain that results from inflammatory processes, such as may arise in the case of infections, arthritis and neoplasia or tumor related hypertrophy. Tumor or cancer associated pain is, therefore, considered to fall within the category of inflammatory pain.

Reference to "neuropathic pain" or "inflammatory pain" includes reference to a neuropathic or inflammatory component of nociceptive pain.

The method according to the present invention to induces an analgesic response to neuropathic and/or inflammatory pain being suffered by a mammalian, preferably human, patient. A patient, in this context, is also referred to as a "subject", "target" or "recipient". In this context the terms "analgesia" and "analgesic response" are intended to describe a state of reduced sensibility to pain, which preferably occurs without overt sedation and preferably without an effect upon the sense of touch. Preferably, the sensibility to pain is reduced by at least 30%, preferably at least 50%, more preferably at least 70% and particularly preferably at least 85%. In a most preferred aspect of the present invention, the sensibility to the neuropathic pain is completely, or substantially completely, removed. To assess the level of reduction of sensibility to pain associated with the analgesia induced by the methods according to the present invention it is possible to conduct tests such as the short form McGill pain questionnaire and/or visual analogue scales for pain intensity and/or verbal rating scales for pain intensity and/or measurement of tactile allodynia using von Frey hairs or similar device. These tests are standard tests within the art and would be well known to the skilled person.

Accordingly, one aspect of the present invention contemplates a method for inducing an analgesic response to neuropathic or inflammatory pain in a mammal comprising administering to the subject an amount of flupirtine or a pharmaceutically acceptable salt, derivative, homolog or analog thereof effective to reduce the level of or otherwise ameliorate the sensation of pain.

Another aspect of the present invention provides a method of inducing analgesia in a mammal suffering neuropathic or inflammatory pain by administering to the mammal one of an analgesic agent or flupirtine or a pharmaceutically acceptable salt, derivative, homolog or analog thereof concurrently, separately or sequentially with respect to the other of an analgesic agent or flupirtine or a pharmaceutically acceptable salt, derivative, homolog or analog thereof, in an amount effective to reduce the level of or otherwise ameliorate the sensation of pain.

Still another aspect of the present invention contemplates combination therapy such as in the treatment of cancer, inflammation, back pain a neurological condition or a chronic disease or condition or other pathology wherein the treatment of the disease, condition or pathology is conducted in association with pain management using flupirtine or a pharmaceutically acceptable salt, derivative, homolog or analog thereof and optionally in addition to an analgesic agent.

In both cases, the analgesic effect is preferably without overt sedation or the other side effects of flupirtine or the analgesic agent.

By the term "overt sedation" it is intended to convey that the methods (and compositions) of the invention do not result in practically meaningful sedation of the patient or subject being treated, i.e. significant, visible or apparent drowsiness or unconsciousness of the patient being treated. Thus, the treatment methods of the invention do not result in sleepiness or drowsiness in the patient that interfere with, or inhibit, the activities associated with day to day living, such as driving a motor vehicle or operating machinery for human subjects, or feeding and grooming for animal subjects.

Collectively, the flupirtine or pharmaceutically acceptable salt, derivative, homolog or analog thereof and the other analgesic agent will be referred to as the "active agents". A synergistically effective amount of flupirtine or a pharmaceutically acceptable salt, derivative, homolog or analog thereof, when administered concurrently, separately or sequentially with an analgesic agent such as an opioid may restore or improve opioid responsiveness to neuropathic or inflammatory pain. The active agents may be administered either as a combined form, i.e. a single composition containing the active agents, or as discrete dosages. The active agents will preferably be administered within a time frame allowing the desired additive or synergistic analgesic effect to be achieved. That is, the timing of administration should allow each of the active agents or their active metabolites to simultaneously be present within the patient within their respective therapeutic concentration ranges. The time between the delivery of the agents is between seconds, minutes, hours, days or weeks.

The term "analgesic agent" is intended to encompass known and as yet unknown compounds (including pharmaceutically acceptable salts, derivatives, homologs or analogs thereof) that are effective for treatment of pain in mammals, including opioids and compounds such as aspirin, indomethacin, naproxen, fenoprofen, sulindac, diclofenac, indoprofen, nitroglycerin, propanolol, valproate, timolol, atenolol, alprenolol, cimetidinze, clonidine, imipramine, levodopa, chloropromazine, reserpine, methyl-dopa, dihydroxyphenylalanine, provaloxyloxyethyl ester of alpha-methyldopa hydrochloride, theophylline, calcium gluconate, ferrous lactate, vincamine, diazepam, phenoxybenzamine, blocking agents, paracetamol; NSAIDs such as ibuprofen, indomethacin and phenylbutazone; the opioids; tricyclic antidepressants such as amitryptyline; anticonvulsants such as carbamazepine and sodium valproate; local anaesthetics such as lignocaine, mexiletine; NMDA antagonists such as dextromethorphan or ketamine; neurosteroid analgesics such as alphadolone; and GABA analogs such as GABApentin and pre-gabalin and pharmaceutically acceptable salts, derivatives, homologs or analogs thereof. One of the actions of the GABA analogs, such as GABApentin and pre-gabalin, act on the alpha(2)delta subunit of voltage-dependent calcium channels. The term is intended to particularly encompass analgesics in relation to which dose limiting side effects are associated, and especially those associated with induction of sedation. Particularly preferred other analgesic agents are the opioids.

GABAergic drugs can also be used in combination with flupirtine for the treatment of neuropathic and inflammatory pain. GABAergic drugs include compounds that enhance the action of gamma aminobutyric acid (GABA) in the central nervous system; these include drugs that act directly on receptors such as baclofen, muscimol, alcohols, neurosteroids and benzodiazepines, drugs such as vigabatrin that cause inhibition of extra neuronal enzymatic breakdown of GABA, drugs such as topiramate that modulate GABA-coupled ion channels and drugs such as tiagabine that inhibit the reuptake of synaptic GABA by neurons and glial cells.

As used herein, opioid compounds (opioids) include any compound that is physiologically acceptable in mammalian systems and is a full or at least partial agonist of an opioid receptor. Opioid compounds are well known and include naturally occurring compounds derived from opium such as codeine, morphine and papavarine as well as derivatives of such compounds that generally have structural similarity as well as other structurally unrelated compounds that agonise an opioid receptor present in a mammalian system. Specific examples of opioid compounds contemplated by the present invention include: fentanyl, oxycodone, codeine, dihydrocodeine, dihydrocodeinone enol acetate, morphine, desomorphine, apomorphine, diamorphine, pethidine, methadone, dextropropoxyphene, pentazocine, dextromoramide, oxymorphone, hydromorphone, dihydromorphine, noscapine, nalbuprhine papaverine, papaveretum, alfentanil, buprenorphine and tramadol and pharmaceutically acceptable salts, derivatives, homologs or analogs thereof.

The phrase "pharmaceutically acceptable salt, derivative, homologs or analogs" is intended to convey any pharmaceutically acceptable tautomer, salt, pro-drug, hydrate, solvate, metabolite or other compound which, upon administration to the subject, is capable of providing (directly or indirectly) the compound concerned or a physiologically (e.g. analgesically) active compound, metabolite or residue thereof. An example of a suitable derivative is an ester formed from reaction of an OH or SH group with a suitable carboxylic acid, for example $C_{1-3}$alkyl-$CO_2H$, and $HO_2C$—$(CH_2)_n$—$CO_2H$ (where n is 1-10 such as 1, 2, 3, 4, 5, 6, 7, 8, 9, 10, but preferably 1-4), and $CO_2H$—$CH_2$phenyl.

Thus, the active compounds may be in crystalline form, either as the free compounds or as solvates (e.g. hydrates). Methods of solvation are generally known within the art.

The salts of the active compounds of the invention are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulfphonic, toluenesulphonic, benzenesulphonic, salicyclic, sulphanilic, aspartic, glutamic, edetic, stearic, palmitic, oleic, lauric, pantothenic, tannic, ascorbic and valeric acids.

The term "pro-drug" is used herein in its broadest sense to include those compounds which can be converted in vivo to the compound of interest (e.g. by enzymatic or hydrolytic cleavage). Examples thereof include esters, such as acetates of hydroxy or thio groups, as well as phosphates and sulphonates. Processes for acylating hydroxy or thio groups are known in the art, e.g. by reacting an alcohol (hydroxy group), or thio group, with a carboxylic acid. Other examples of suitable pro-drugs are described in *Design of Prodrugs*, H. Bundgaard, Elsevier, 1985, the disclosure of which is included herein in its entirety by way of reference.

The term "metabolite" includes any compound into which the active agents can be converted in vivo once administered to the subject. Examples of such metabolites are glucuronides, sulphates and hydroxylates.

It will be understood that active agents as described herein may exist in tautomeric forms. The term "tautomer" is used herein in its broadest sense to include compounds capable of existing in a state of equilibrium between two isomeric forms. Such compounds may differ in the bond connecting two atoms or groups and the position of these atoms or groups in the compound. A specific example is keto-enol tautomerism.

The compounds of the present invention may be electrically neutral or may take the form of polycations, having associated anions for electrical neutrality. Suitable associated anions include sulfate, tartrate, citrate, chloride, nitrate, nitrite, phosphate, perchlorate, halosulfonate or trihalomethylsulfonate.

The active agents may be administered for therapy by any suitable route. It will be understood that the active agents are preferably administered via a route that does not result in overt sedation of the subject. Suitable routes of administration may include oral, rectal, nasal, inhalation of aerosols or particulates, topical (including buccal and sublingual), transdermal, vaginal, intravesical and parenteral (including subcutaneous, intramuscular, intravenous, intrasternal, intrathecal, epidural and intradermal). Preferably, administration of the active agents will be by a route resulting in first presentation of the compound to the stomach of the subject. In a particularly preferred embodiment of the invention, the active agents are administered via an oral route. In another preferred embodiment the active agents are administered by the transdermal route. However it will be appreciated that the preferred route will vary with the condition and age of the subject, the nature of the inflammatory or neuropathic pain being treated, its location within the subject and the judgement of the physician or veterinarian. It will also be understood that individual active agents may be administered by the same or different distinct routes.

As used herein, an "effective amount" refers to an amount of active agent that provides the desired analgesic activity when administered according to a suitable dosing regime. Preferably the amount active agent is an amount that provides the desired analgesic activity without causing overt sedation. Dosing may occur at intervals of several minutes, hours, days, weeks or months. Suitable dosage amounts and regimes can be determined by the attending physician or veterinarian. For example, flupirtine or pharmaceutically acceptable salts, derivatives, homologs or analogs thereof, may be administered to a subject at a rate of between about 0.5 to about 20 mg/kg every from about 1 hour to up to about 50 hours, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 hours, such as 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20 mg/kg. Particularly useful times are from about 6 hours to about 24 hours, such as 6, 7, 8, 9, 10, 11, 12, 13, 14, 15, 16, 17, 18, 19, 20, 21, 22, 23, 24. Even more particular useful times are between from about 12 to about 24 hours. Such as 12, 13, 14, 15, 16, 17, 18, 19, 20, 21, 22, 23 or 24 hours. Dosing of the analgesic agent, such as an opioid, can be determined by the attending physician in accordance with dosing rates in practice. For example, fentanyl can be administered in an amount of about 100 μg whereas morphine may be administered in an amount of 10 mg, also on an hourly basis. The administration amounts may be varied if administration is conducted more or less frequently, such as by continuous infusion, by regular dose every few minutes (e.g. 1, 2, 3 or 4 minutes) or by administration every 5, 10, 20, 30 or 40 minutes (e.g. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 45, 36, 37, 38, 39 or 40 minutes) or every 1, 2, 3, 4, 5, 6, 7, 8, 9, 10, 11, 12, 13, 14, 15, 16, 17, 18, 19, 20, 21, 22, 23 or 24 hours or up to 50 hours such as, for example, 25, 26, 27, 28, 29, 30, 31, 32, 33, 34, 35, 36, 37, 38, 39, 40, 41, 42, 43, 44, 45, 46, 47, 48, 49 or 50 hours. In many instances administration will be conducted simply on the basis of when the patient requires pain relief.

In relation to combination to therapy, flupirtine or its pharmaceutically acceptable salts, derivatives, homolog or analogs thereof and optionally together with an analgesic agent such as an opioid is used to manage pain and induce an analgesic response prior to, during or following treatment of a disease, condition or pathology such as cancer, inflammation, back pain or a neurological condition.

In one particular embodiment, flupirtine or its pharmaceutically acceptable salts, derivatives, homologs or analogs thereof and optionally an analgesic agent such as a opioid is used prior to, during or following cancer treatment. Examples of cancers which may be treated using this approach include but are not limited to ABL1 protooncogene, AIDS Related Cancers, Acoustic Neuroma, Acute Lymphocytic Leukaemia, Acute Myeloid Leukaemia, Adenocystic carcinoma, Adrenocortical Cancer, Agnogenic myeloid metaplasia, Alopecia, Alveolar soft-part sarcoma, Anal cancer, Angiosarcoma, Aplastic Anaemia, Astrocytoma, Ataxia-telangiectasia, Basal Cell Carcinoma (Skin), Bladder Cancer, Bone Cancers, Bowel cancer, Brain Stem Glioma, Brain and CNS Tumors, Breast Cancer, CNS tumors, Carcinoid Tumors, Cervical Cancer, Childhood Brain Tumors, Childhood Cancer, Childhood Leukaemia, Childhood Soft Tissue Sarcoma, Chondrosarcoma, Choriocarcinoma, Chronic Lymphocytic Leukaemia, Chronic Myeloid Leukaemia, Colorectal Cancers, Cutaneous T-Cell Lymphoma, Dermatofibrosarcoma-protuberans, Desmoplastic-Small-Round-Cell-Tumor, Ductal Carcinoma, Endocrine Cancers, Endometrial Cancer, Ependymoma, Esophageal Cancer, Ewing's Sarcoma, Extra-Hepatic Bile Duct Cancer, Eye Cancer, Eye: Melanoma, Retinoblastoma, Fallopian Tube cancer, Fanconi Anaemia, Fibrosarcoma, Gall Bladder Cancer, Gastric Cancer, Gastrointestinal Cancers, Gastrointestinal-Carcinoid-Tumor, Genitourinary Cancers, Germ Cell Tumors, Gestational-Trophoblastic-Disease, Glioma, Gynaecological Cancers, Haematological Malignancies, Hairy Cell Leukaemia, Head and Neck Cancer, Hepatocellular Cancer, Hereditary Breast Cancer, Histiocytosis, Hodgkin's Disease, Human Papillomavirus, Hydatidiform mole, Hypercalcemia, Hypopharynx Cancer, IntraOcular Melanoma, Islet cell cancer, Kaposi's sarcoma, Kidney Cancer, Langerhan's-Cell-Histiocytosis, Laryngeal Cancer, Leiomyosarcoma, Leukaemia, Li-Fraumeni Syndrome, Lip Cancer, Liposarcoma, Liver Cancer, Lung Cancer, Lymphedema, Lymphoma, Hodgkin's Lymphoma, Non-Hodgkin's Lymphoma, Male Breast Cancer, Malignant-Rhabdoid-Tumor-of-Kidney, Medulloblastoma, Melanoma, Merkel Cell Cancer, Mesothelioma, Metastatic Cancer, Mouth Cancer, Multiple Endocrine Neoplasia, Mycosis Fungoides, Myelodysplastic Syndromes, Myeloma, Myeloproliferative Disorders, Nasal Cancer, Nasopharyngeal Cancer, Nephroblastoma, Neuroblastoma, Neurofibromatosis, Nijmegen Breakage Syndrome, Non-Melanoma Skin Cancer, Non-Small-Cell-Lung-Cancer-(NSCLC), Ocular Cancers, Oesophageal Cancer, Oral cavity Cancer, Oropharynx Cancer, Osteosarcoma, Ostomy Ovarian Cancer, Pancreas Cancer, Paranasal Cancer, Parathyroid Cancer, Parotid Gland Cancer, Penile Cancer, Peripheral-Neuroectodermal-Tumors, Pituitary Cancer, Polycythemia vera, Prostate Cancer, Rare-cancers-and-associated-disorders, Renal Cell Carcinoma, Retinoblastoma, Rhabdomyosarcoma, Rothmund-Thomson Syndrome, Salivary Gland Cancer, Sarcoma, Schwannoma, Sezary syndrome, Skin Cancer, Small Cell Lung Cancer (SCLC), Small Intestine Cancer, Soft Tissue Sarcoma, Spinal Cord Tumors, Squamous-Cell-Carcinoma-(skin), Stomach Cancer, Synovial sarcoma, Testicular Cancer, Thymus Cancer, Thyroid Cancer, Transitional-Cell-Cancer-(bladder), Transitional-Cell-Cancer-(renal-pelvis-/-ureter), Trophoblastic Cancer, Urethral Cancer, Urinary System Cancer, Uroplakins, Uterine sarcoma, Uterus Cancer, Vaginal Cancer, Vulva Cancer, Waldenstrom's-Macroglobulinemia or Wilms' Tumor. In some cases, the treatment potential of flupirtine and optionally an opioid and/or anti-cancer agent may also include a pronopshine.

Accordingly, this aspect of the present invention contemplates a treatment protocol for cancer in a subject, said protocol comprising the steps of administering to said subject, an effective amount of an anti-cancer agent and an amount of flupirtine or a pharmaceutically acceptable salt, derivative, homolog or analog thereof effective to reduce the level of or otherwise ameliorate the sensation of pain. The cancer may include any of those listed above. Administration of the anti-cancer agent may be sequential or simultaneous or independent of the flupirtine.

In another embodiment, combination therapy is in relation to inflammation. Examples of inflammatory conditions include but are not limited to as used herein "inflammatory diseases and disorders" encompass those disease and disorders which result in a response of redness, swelling, pain, and a feeling of heat in certain areas that is meant to protect tissues affected by injury or disease. Inflammatory diseases which can be treated using the methods of the present invention, include, without being limited to, acne, angina, arthritis, aspiration pneumonia, disease, empyema, gastroenteritis, inflammation, intestinal flu, NEC, necrotizing enterocolitis, pelvic inflammatory disease, pharyngitis, PID, pleurisy, raw throat, redness, rubor, sore throat, stomach flu and urinary tract infections, Chronic Inflammatory Demyelinating Polyneuropathy, Chronic Inflammatory Demyelinating Polyradiculoneuropathy, Chronic Inflammatory Demyelinating Polyneuropathy, Chronic Inflammatory Demyelinating Polyradiculoneuropathy.

Accordingly, this aspect of the present invention contemplates a treatment protocol for inflammation in a subject, said protocol comprising the steps of administering to said subject, an effective amount of an anti-inflammatory agent and an amount of flupirtine or a pharmaceutically acceptable salt, derivative, homolog or analog thereof effective to reduce the level of or otherwise ameliorate the sensation of pain. The inflammatory disease may include any of those listed above. Administration of the anti-inflammatory agent may be sequential or simultaneous or independent of the flupirtine.

In yet another embodiment, combination therapy is in relation to neurological conditions. Examples of neurological conditions include but are not limited to neural injury, neurological diseases, severe burns, severe trauma, chronic non-neurological diseases, chronic infections, chronic corticosteroid administration, AIDS, and the like. Neural injuries include acute brain injuries, traumatic brain injuries, closed head injuries, stroke, and the like. Neurological diseases include chronic neurodegenerative diseases such as Alzheimer's disease, Parkinson's disease, Huntington's disease, multiple sclerosis, and the like. The chronic corticosteroid administration may be associated with anti-neoplastic therapy, anti-inflammatory therapy, immunosuppression, and the like.

Accordingly, this aspect of the present invention contemplates a treatment protocol for a neurological condition in a subject, said protocol comprising the steps of administering to said subject, an effective amount of an agent used to treat a neurological condition and an amount of flupirtine or a pharmaceutically acceptable salt, derivative, homolog or analog thereof effective to reduce the level of or otherwise ameliorate the sensation of pain. The neurological condition may include any of those listed above. Administration of an agent used to treat a neurological disease may be sequential or simultaneous or independent of the flupirtine.

In a further embodiment, combination therapy is in relation to reducing pain during the treatment of or amelioration of symptoms of any one or more of the following diseases which cause neuropathic pain or which have a neuropathic pain component: Abdominal Wall Defect, Abdominal Migraine, Achondrogenesis, Achondrogenesis Type IV, Achondrogenesis Type III, Achondroplasia, Achondroplasia Tarda, Achondroplastic Dwarfism, Acquired Immunodeficiency Syndrome (AIDS), Acute Intermittant Porphyria, Acute Porphyrias, Acute Shoulder Neuritis, Acute Toxic Epidermolysis, Adiposa Dolorosa, Adrenal Neoplasm, Adrenomyeloneuropathy, Adult Dermatomyositis, Amyotrophic Lateral Sclerosis, Amyotrophic Lateral Sclerosis-Polyglucosan Bodies, AN, AN 1, AN 2, Anal Rectal Malformations, Anal Stenosis, Arachnitis, Arachnoiditis Ossificans, Arachnoiditis, Arteritis Giant Cell, Arthritis, Arthritis Urethritica, Ascending Paralysis, Astrocytoma Grade I (Benign), Astrocytoma Grade II (Benign), Athetoid Cerebral Palsy, Barrett Esophagus, Barrett Ulcer, Benign Tumors of the Central Nervous System, Bone Tumor-Epidermoid Cyst-Polyposis, Brachial Neuritis, Brachial Neuritis Syndrome, Brachial Plexus Neuritis, Brachial-Plexus-Neuropathy, Brachiocephalic Ischemia, Brain Tumors, Brain Tumors Benign, Brain Tumors Malignant, Brittle Bone Disease, Bullosa Hereditaria, Bullous CIE, Bullous Congenital Ichthyosiform Erythroderma, Bullous Ichthyosis, Bullous Pemphigoid, Burkitt's Lymphoma, Burkitt's Lymphoma African type, Burkitt's Lymphoma Non-african type, Calcaneal Valgus, Calcaneovalgus, Cavernous Lymphangioma, Cavernous Malformations, Central Form Neurofibromatosis, Cervical Spinal Stenosis, Cervical Vertebral Fusion, Charcot's Disease, Charcot-Marie-Tooth, Charcot-Marie-Tooth Disease, Charcot-Marie-Tooth Disease Variant, Charcot-Marie-Tooth-Roussy-Levy Disease, Childhood Dermatomyositis, Chondrodysplasia Punctata, Chondrodystrophia Calcificans Congenita, Chondrodystrophia Fetalis, Chondrodystrophic Myotonia, Chondrodystrophy, Chondrodystrophy with Clubfeet, Chondrodystrophy Epiphyseal, Chondrodystrophy Hyperplastic Form, Chondroectodermal Dysplasias, Chondrogenesis Imperfecta, Chondrohystrophia, Chondroosteodystrophy, Chronic Adhesive Arachnoiditis, Chronic Idiopathic Polyneuritis (CIP), Chronic Inflammatory Demyelinating Polyneuropathy, Chronic Inflammatory Demyelinating Polyradiculoneuropathy, Cicatricial Pemphigoid, Complex Regional Pain Syndrome, Congenital Cervical Synostosis, Congenital Dysmyelinating Neuropathy, Congenital Hypomyelinating Polyneuropathy, Congenital Hypomyelination Neuropathy, Congenital Hypomyelination, Congenital Hypomyelination (Onion Bulb) Polyneuropathy, Congenital Ichthyosiform Erythroderma, Congenital Tethered Cervical Spinal Cord Syndrome, Cranial Arteritis, Crohn's Disease, Cutaneous Porphyrias, Degenerative Lumbar Spinal Stenosis, Demyelinating Disease, Diabetes Mellitus Diabetes Insulin Dependent, Diabetes Mellitus, Diabetes Mellitus Addison's Disease Myxedema, Discoid Lupus, Discoid Lupus Erythematosus, Disseminated Lupus Erythematosus, Disseminated Neurodermatitis, Disseminated Sclerosis, EDS Kyphoscoliotic, EDS Kyphoscoliosis, EDS Mitis Type, EDS Ocular-Scoliotic, Elastosis Dystrophica Syndrome, Encephalofacial Angiomatosis, Encephalotrigeminal Angiomatosis, Enchondromatosis with Multiple Cavernous Hemangiomas, Endemic Polyneuritis, Endometriosis, Eosinophilic Fasciitis, Epidermolysis Bullosa, Epidermolysis Bullosa Acquisita, Epidermolysis Bullosa Hereditaria, Epidermolysis Bullosa Letalias, Epidermolysis Hereditaria Tarda, Epidermolytic Hyperkeratosis, Epidermolytic Hyperkeratosis (Bullous CIE), Familial Lumbar Stenosis, Familial Lymphedema Praecox, Fibromyalgia, Fibromyalgia-Fibromyositis, Fibromyositis, Fibrositis, Fibrous Ankylosis of Multiple Joints, Fibrous Dysplasia, Fragile X syndrome, Generalized Fibromatosis, Guillain-Barre Syndrome, Hemangiomatosis Chondrodystrophica, Hereditary Sensory and Autonomic Neuropathy Type I, Hereditary Sensory and Autonomic Neuropathy Type II, Hereditary Sensory and Autonomic Neuropathy Type III, Hereditary Sensory Motor Neuropathy, Hereditary Sensory Neuropathy type I, Hereditary Sensory Neuropathy Type I, Hereditary Sensory Neuropathy Type II, Hereditary Sensory Neuropathy Type III, Hereditary Sensory Radicular Neuropathy Type I, Hereditary Sensory Radicular Neuropathy Type I, Hereditary Sensory Radicular Neuropathy Type II, Herpes Zoster, Hodgkin Disease, Hodgkin's Disease, Hodgkin's Lymphoma, Hyperplastic Epidermolysis Bullosa, Hypertrophic Interstitial Neuropathy, Hypertrophic Interstitial Neuritis, Hypertrophic Interstitial Radiculoneuropathy, Hypertrophic Neuropathy of Refsum, Idiopathic Brachial Plexus Neuropathy, Idiopathic Cervical Dystonia, Juvenile (Childhood) Dermatomyositis (JDMS), Juvenile Diabetes, Juvenile Rheumatoid Arthritis, Pes Planus, Leg Ulcer, Lumbar Canal Stenosis, Lumbar Spinal Stenosis, Lumbosacral Spinal Stenosis, Lupus, Lupus, Lupus Erythematosus, Lymphangiomas, Mononeuritis Multiplex, Mononeuritis Peripheral, Mononeuropathy Peripheral, Monostotic Fibrous Dysplasia, Multiple Cartilaginous Enchondroses, Multiple Cartilaginous Exostoses, Multiple Enchondromatosis, Multiple Myeloma, Multiple Neuritis of the Shoulder Girdle, Multiple Osteochondromatosis, Multiple Peripheral Neuritis, Multiple Sclerosis, Musculoskeletal Pain Syndrome, Neuropathic Amyloidosis, Neuropathic Beriberi, Neuropathy of Brachialpelxus Syndrome, Neuropathy Hereditary Sensory Type I, Neuropathy Hereditary Sensory Type II, Nieman Pick disease Type A (acute neuronopathic form), Nieman Pick disease Type B, Nieman Pick Disease Type C (chronic neuronopathic form), Non-Scarring Epidermolysis Bullosa, Ochronotic Arthritis, Ocular Herpes, Onion-Bulb Neuropathy, Osteogenesis Imperfect, Osteogenesis Imperfecta, Osteogenesis Imperfecta Congenita, Osteogenesis Imperfecta Tarda, Peripheral Neuritis, Peripheral Neuropathy, Perthes Disease, Polyarteritis Nodosa, Polymyalgia Rheumatica, Polymyositis and Dermatomyositis, Polyneuritis Peripheral, Polyneuropathy Peripheral, Polyneuropathy and Polyradiculoneuropathy, Polyostotic Fibrous Dysplasia, Polyostotic Sclerosing Histiocytosis, Postmyelographic Arachnoiditis, Primary Progressive Multiple Sclerosis, Psoriasis, Radial Nerve Palsy, Radicular Neuropathy Sensory, Radicular Neuropathy Sensory Recessive, Reflex Sympathetic Dystrophy Syndrome, Relapsing-Remitting Multiple Sclerosis, Sensory Neuropathy Hereditary Type I, Sensory Neuropathy Hereditary Type II, Sensory Neuropathy Hereditary Type I, Sensory Radicular Neuropathy, Sensory Radicular Neuropathy Recessive, Sickle Cell Anemia, Sickle Cell Disease, Sickle Cell-Hemoglobin C Disease, Sickle Cell-Hemoglobin D Disease, Sickle Cell-Thalassemia Disease, Sickle Cell Trait, Spina Bifida, Spina Bifida Aperta, Spinal Arachnoiditis, Spinal Arteriovenous Malformation, Spinal Ossifying Arachnoiditis, Spinal Stenosis, Stenosis of the Lumbar Vertebral Canal, Still's Disease, Syringomyelia, Systemic Sclerosis, Talipes Calcaneus, Talipes Equinovarus, Talipes Equinus, Talipes Varus, Talipes Valgus, Tandem Spinal Stenosis, Temporal Arteritis/Giant Cell Arteritis, Temporal Arteritis, Tethered Spinal Cord Syndrome, Tethered Cord Malformation Sequence, Tethered Cord Syndrome, Tethered Cervical Spinal Cord Syndrome, Thalamic Pain Syndrome, Thalamic Hyperesthetic Anesthesia, Trigeminal Neuralgia, Variegate Porphyria, Vertebral Ankylosing Hyperostosis amongst others.

Accordingly, still another aspect of the present invention contemplates a treatment protocol for a disease condition in a subject, said protocol comprising the steps of administering to said subject, an effective amount of an a disease condition and an amount of flupirtine or a pharmaceutically acceptable salt, derivative, homolog or analog thereof effective to reduce the level of or otherwise ameliorate the sensation of pain. The disease condition may include any of those listed above. Administration of the disease condition may be sequential or simultaneous or independent of the flupirtine.

The present invention also relates to compositions comprising flupirtine or a pharmaceutically acceptable salt, derivative, homolog or analog thereof, optionally with another analgesic agent such as an opioid, together with one or more pharmaceutically acceptable additives and optionally other medicaments. The pharmaceutically acceptable additives may be in the form of carriers, diluents, adjuvants and/or excipients and they include all conventional solvents, dispersion agents, fillers, solid carriers, coating agents, antifungal or antibacterial agents, dermal penetration agents, surfactants, isotonic and absorption agents and slow or controlled release matrices. The active agents may be presented in the form of a kit of components adapted for allowing concurrent, separate or sequential administration of the active agents. Each carrier, diluent, adjuvant and/or excipient must be "pharmaceutically acceptable" in the sense of being compatible with the other ingredients of the composition and physiologically tolerated by the subject. The compositions may conveniently be presented in unit dosage form and may be prepared by methods well known in the art of pharmacy. Such methods include the step of bringing into association the active ingredient with the carrier, which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous phase or non-aqueous liquid; or as an oil-in-water liquid emulsion or a water-in-oil emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant, sodium starch glycollate, cross-linked povidone, cross-linked sodium carboxymethyl cellulose) surface-active or dispersing agent. Moulded tablets may be made my moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for parenteral administration include aqueous and non-aqueous isotonic sterile injection solutions which may contain anti-oxidants, buffers, bacteriostats and solutes which render the composition isotonic with the blood of the intended subject; and aqueous and non-aqueous sterile suspensions which may include suspended agents and thickening agents. The compositions may be presented in a unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compositions suitable for topical administration to the skin, i.e. transdermal administration, may comprise the active agents dissolved or suspended in any suitable carrier or base and may be in the form of lotions, gels, creams, pastes, ointments and the like. Suitable carriers may include mineral oil, propylene glycol, waxes, polyoxyethylene and long chain alcohols. Transdermal devices, such as patches may also be used and may comprise a microporous membrane made from suitable material such as cellulose nitrate/acetate, propylene and polycarbonates. The patches may also contain suitable skin adhesive and backing materials.

The active compounds of the present invention may also be presented as implants, which may comprise a drug bearing polymeric device wherein the polymer is biocompatible and non-toxic. Suitable polymers may include hydrogels, silicones, polyethylenes and biodegradable polymers.

The compounds of the subject invention may be administered in a sustained (i.e. controlled) or slow release form. A sustained release preparation is one in which the active ingredient is slowly released within the body of the subject once administered and maintains the desired drug concentration over a minimum period of time. The preparation of sustained release formulations is well understood by persons skilled in the art. Dosage forms may include oral forms, implants and transdermal forms. For slow release administration, the active ingredients may be suspended as slow release particles or within liposomes, for example.

The pharmaceutical compositions of the present invention may be packaged for sale with other active agents or alternatively, other active agents may be formulated with flupirtine or its pharmaceutical salts, derivatives, homologs or analogs thereof and optionally an analgesic agent such as an opioid.

Thus, a further particular aspect of the present invention provides a system for the controlled release of flupirtine or a pharmaceutically acceptable salt, derivative, homolog or analog thereof and optionally an opioid, alone or together with another analgesic or active agent, wherein the system comprises:

(a) a deposit-core comprising an effective amount of the active substance and having defined geometric form, and (b) a support-platform applied to the deposit-core, wherein the deposit-core contains at least the active substance, and at least one member selected from the group consisting of:

(i) a polymeric material which swells on contact with water or aqueous liquids and a gellable polymeric material wherein the ratio of the swellable polymeric material to the gellable polymeric material is in the range 1:9 to 9:1, and (ii) a single polymeric material having both swelling and gelling properties, and wherein the support-platform is an elastic support, applied to the deposit-core so that it partially covers the surface of the deposit-core and follows changes due to hydration of the deposit-core and is slowly soluble and/or slowly gellable in aqueous fluids.

The support-platform may comprise polymers such as hydroxypropylmethylcellulose, plasticizers such as a glyceride, binders such as polyvinylpyrrolidone, hydrophilic agents such as lactose and silica, and/or hydrophobic agents such as magnesium stearate and glycerides. The polymer(s) typically make up 30 to 90% by weight of the support-platform, for example about 35 to 40%. Plasticizer may make up at least 2% by weight of the support platform, for example about 15 to 20%. Binder(s), hydrophilic agent(s) and hydrophobic agent(s) typically total up to about 50% by weight of the support platform, for example about 40 to 50%.

The tablet coating may contain one or more water insoluble or poorly soluble hydrophobic excipients. Such excipients may be selected from any of the known hydrophobic cellulosic derivatives and polymers including alkylcellulose, e.g. ethylcellulose, hydroxypropyl cellulose, hydroxypropylmethyl cellulose, carboxymethyl cellulose, and derivatives thereof; polymethacrylic polymers, polyvinyl acetate and cellulose acetate polymers; fatty acids or their esters or salts; long chain fatty alcohols; polyoxyethylene alkyl ethers; polyoxyethylene stearates; sugar esters; lauroyl macrogol-32 glyceryl, stearoyl macrogol-32 glyceryl, and the like. Hydroxypropylmethyl cellulose materials are preferably selected from those low Mw and low viscosity materials such as E-Type methocel, and 29-10 types as defined in the USP.

Other agents or excipients that provide hydrophobic quality to coatings may be selected from any waxy substance known for use as tablet excipients. Preferably they have a HLB value of less than 5, and more preferably about 2. Suitable hydrophobic agents include waxy substances such as carnauba wax, paraffin, microcrystalline wax, beeswax, cetyl ester wax and the like; or non-fatty hydrophobic substances such as calcium phosphate salts, e.g. dibasic calcium phosphate.

Preferably the coating contains a calcium phosphate salt, glyceryl behenate, and polyvinyl pyrollidone, or mixtures thereof, and one or more adjuvants, diluents, lubricants or fillers.

Preferred components in the coating are as follows, with generally suitable percentage amounts expressed as percentage weight of the coating.

Polyvinyl pyrollidone (Povidone) is preferably present in amounts of about 1 to 25% by weight or the coating, more particularly 4 to 12%, e.g. 6 to 8%.

Glyceryl behenate is an ester of glycerol and behenic acid (a C22 fatty acid). Glyceryl behenate may be present as its mono-, di-, or tri-ester form, or a mixture thereof. Preferably it has an HLB value of less than 5, more preferably approximately 2. It may be present in amounts of about 5 to 85% by weight of the coating, more particularly from 10 to 70% by weight, and in certain preferred embodiments from 30 to 50%.

Calcium phosphate salt may be the dibasic calcium phosphate dihydrate and may be present in an amount of about 10 to 90% by weight of the coating, preferably 20 to 80%, e.g. 40 to 75%.

The coating may contain other common tablet excipients such as lubricants, colourants, binders, diluents, glidants and taste-masking agents or flavourants.

Examples of excipients include colourants such a ferric oxide, e.g. yellow ferric oxide; lubricants such as magnesium stearate; and glidants such as silicon dioxide, e.g. colloidal silicon dioxide. Yellow ferric oxide may be used in amounts of about 0.01 to 0.5% by weight based on the coating; magnesium stearate may be present in amounts of 1 to 20% by weight of the coating, more preferably 2 to 10%, e.g. 0.5 to 1.0%; and colloidal silica may be used in amounts of 0.1 to 20% by weight of the coating, preferably 1 to 10%, more preferably 0.25 to 1.0%.

The core comprises in addition to a drug substance, a disintegrating agent or mixtures of disintegrating agents used in immediate release formulations and well know to persons skilled in the art. The disintegrating agents useful in the exercise of the present invention may be materials that effervesce and or swell in the presence of aqueous media thereby to provide a force necessary to mechanically disrupt the coating material.

Preferably a core contains, in addition to the drug substance, cross-linked polyvinyl pyrollidone and croscarmellose sodium.

The following is a list of preferred core materials. The amounts are expressed in terms of percentage by weight based on the weight of the core.

Cross-linked polyvinyl pyrollidone is described above and is useful as a disintegrating agent, and may be employed in the core in the amounts disclosed in relation to the core.

Croscarmellose sodium is an internally cross-linked sodium carboxymethyl cellulose (also known as Ac-Di-Sol) useful as a disintegrating agent.

Disintegrating agents may be used in amounts of 5 to 30% by weight based on the core. However, higher amounts of certain disintegrants can swell to form matrices that may modulate the release of the drug substance. Accordingly, particularly when rapid release is required after the lag time it is preferred that the disintegrants is employed in amounts of up to 10% by weight, e.g. about 5 to 10% by weight.

The core may additionally comprise common tablet excipients such as those described above in relation to the coating material. Suitable excipients include lubricants, diluents and fillers, including but not limited to lactose (for example the mono-hydrate), ferric oxide, magnesium stearates and colloidal silica.

Lactose monohydrate is a disaccharide consisting of one glucose and one galactose moiety. It may act as a filler or diluent in the tablets of the present invention. It may be present in a range of about 10 to 90%, preferably from 20 to 80%, and in certain preferred embodiments from 65 to 70%.

As stated above, it is an important aspect of the present invention that core is correctly located within the coating to ensure that a tablet has the appropriate coating thickness.

In this way, lag times will be reliable and reproducible, and intra-subject and inter-subject variance in bioavailability can be avoided. It is advantageous to have a robust in process control to ensure that tablets in a batch contain cores having the appropriate geometry in relation to the coating. Controls can be laborious in that they require an operator to remove random samples from a batch and to cut them open to physically inspect the quality of the core (i.e. whether it is intact, and whether it is correctly located). Furthermore, if a significant number of tablets from the sample fail, a complete batch of tablets may be wasted. Applicant has found that if one adds to the core a strong colourant such as iron oxide, such that the core visibly contrasts with the coating when as strong light is shone on the tablet, it is possible for any faults in the position or integrity of the core to be picked up automatically by a camera appropriately located adjacent a tabletting machine to inspect tablets as they are ejected therefrom.

In another embodiment, a multiparticulate release flupirtine composition for oral administration is provided. The formulation is made by complexing flupirtine or a pharmaceutically acceptable salt, derivative, homolog or analog thereof optionally together with an opioid and/or other analgesic or active agent with an ion-exchange resin in the form of small particles, typically less than 150 microns. To prepare a multiparticulate formulation, one or more of the following types of particles are formulated into a final dosage form: (a) Immediate release particles, prepared by coating drug-containing particles with a polymer that is insoluble in the neutral medium of saliva, but dissolves in the acid environment of the stomach; (b) Enteric coated particles, prepared by coating drug-containing particles with a polymer that is insoluble in the acidic environment of the stomach but dissolves in the neutral environment of the small intestines; (c) Extended release particles, prepared by coating drug-containing particles with a polymer that forms water insoluble but water permeable membrane; (d) Enteric coated-extended release particles, prepared by coating extended release drug particles with an enteric coating; (e) Delayed release particles, prepared by coating drug-containing particles with a polymer that is insoluble in the acidic environment of the stomach and the environment of the upper small intestines, but dissolves in the lower small intestines or upper large intestines.

Still another aspect of the present invention provides a composition comprising: (a) a flupirtine or a pharmaceutically acceptable salt, derivative, homolog or analog thereof; (b) an active component having a delayed time of release; and (c) an immediate release opioid removal component.

The present invention further provides a method for the delivery of the inventive composition to a subject, the method comprising the step of administering the composition to the subject orally, transdermally, or subdermally, wherein the composition comprises components (a), (b), and (c) as defined above.

The present invention creates a tamper-proof narcotic delivery system that provides for full delivery of narcotic medication and for analgesic action on legitimate patients while at the same time effectively eliminating the problem of tampering by diversion, adulteration, or pulverization of the medication for abuse by addicts. The composition and method of the invention are of value to those practiced in the medical arts and simultaneously possess no value or utility to individuals seeking to abuse or profit from the abuse of such analgesics.

The opioid may be alfentanil, allylprodine, alphaprodine, anileridine, benzylmorphine, benzitramide, bupernorphine, butorphanol, clonitazene, codeine, cyclazocine, desomorphine, dextromoramide, dexocine, diampromide, dihydrocodeine, dihydromorphine, dimenoxadol, dimepheptanol, dimethylthiambutene, dioxaphetyl, butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof or mixtures thereof.

Reference to morphine or other opioids includes oral and slow release agents. For example, kapanol is a slow release morphine and ordine is a oral morphine.

The opioid may be either an immediate release agonist or an agonist having a delayed time of release.

It should be understood that in addition to the ingredients particularly mentioned above, the compositions of the present invention may include other agents conventional in the art, having regard to the type of composition in question. For example, agents suitable for oral administration may include such further agents as binders, sweetners, thickeners, flavouring agents, disintegrating agents, coating agents, preservatives, lubricants and/or time delay agents.

In addition, other analgesic compounds or other active ingredients such as anti-cancer compounds may be included. Examples of anti-cancer compounds include anti-metabolites, anti-tumor antibiotics, mitotic inhibitors, steroids, sex hormones, alkylating agents, nitrogen mustards, nitrosources, hormone agonists, and microtubule inhibitors.

Anti-metabolites interfere with the body's chemical processes, such as protein or DNA synthesis required for cell growth and reproduction. Anti-metabolite drugs can prevent cell division which is a requirement in cancer treatment. Examples include Azaserine, D-Cycloserine, Mycophenolic acid, Trimethoprim, 5-fluorouracil, capecitabine, methotrexate, gemcitabine, cytarabine (ara-C) and fludarabine.

Anti-tumor antibiotics interfere with DNA by stopping enzymes and mitosis or altering the membranes that surround cells. These agents work in all phases of the cell cycle. Thus, they are widely used for a variety of cancers. Examples of anti-tumor antibiotics include dactinomycin, daunorubicin, doxorubicin (Adriamycin), idarubicin, and mitoxantrone.

Mitotic inhibitors are plant alkaloids and other compounds derived from natural products. They can inhibit, or stop, mitosis or inhibit enzymes for making proteins needed for reproduction of the cell. These work during the M phase of the cell cycle. Examples of mitotic inhibitors include paclitaxel, docetaxel, etoposide (VP-16), vinblastine, vincristine, and vinorelbine.

Steroids are natural hormones and hormone-like drugs that are useful in treating some types of cancer (such as but not limited to lymphoma, leukemias and multiple myeloma) as well as other illnesses. When these drugs are used to kill cancer cells or slow their growth, they are considered chemotherapeutic drugs. They are often combined with other types of chemotherapy drugs to increase their effectiveness. Examples include prednisone and dexamethasone.

Sex hormones, or hormone-like drugs, alter the action or production of female or male hormones. They are used to slow the growth of breast, prostate, and endometrial (lining of the uterus) cancers, which normally grow in response to hormone levels in the body. Examples include anti-estrogens (tamoxifen, fulvestrant), aromatase inhibitors (anastrozole, letrozole), progestins (megestrol acetate), anti-androgens (bicalutamide, flutamide), and LHRH agonists (leuprolide, goserelin).

Alkylating agents work directly on DNA to prevent the cancer cell from reproducing. As a class of drugs, these agents are not phase-specific (in other words, they work in all phases of the cell cycle). These drugs are active against chronic leukemias, non-Hodgkin's lymphoma, Hodgkin's disease, multiple myeloma, and certain cancers of the lung, breast, and ovary. Examples of alkylating agents include busulfan, cisplatin, carboplatin, chlorambucil, cyclophosphamide, ifosfamide, dacarbazine (DTIC), mechlorethamine (nitrogen mustard), and melphalan.

Nitrogen mustard in the form of its crystalline hydrochloride it is used as a drug in the treatment of Hodgkin's disease, non-Hodgkin's lymphomas and brain tumors. Nitrogen mustards cause mutations in the genetic material of cells, thereby disrupting mitosis, or cell division. Cells vary in their susceptibility to nitrogen mustards, with rapidly proliferating tumor and cancer cells most sensitive; bone marrow, which produces red blood cells, is also sensitive, and depression of red blood cell production is a frequent side effect of nitrogen mustard therapy. The nitrogen mustards also suppress the immune response. Other types include the aromatic mustards melphalan and chlorambucil.

Nitrosoureas act in a similar way to alkylating agents. They interfere with enzymes that help repair DNA. These agents are able to travel to the brain so they are used to treat brain tumors as well as non-Hodgkin's lymphomas, multiple myeloma, and malignant melanoma. Examples of nitrosoureas include carmustine (BCNU) and lomustine (CCNU).

Examples of hormone agonists include Leuprolide (Lupron, Viadur, Eligard) such as for prostate cancer, Goserelin (Zoladex) for breast and prostate cancers and Triptorelin (Trelstar) for ovarian and prostate cancers and nafarelin acetate (Synarel).

Microtubule inhibitors include "Vinca" alkaloids, taxoids and benzimidazoles. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES).

For the treatment of chronic disease conditions, such as cancer, the formulations may also include compounds which assist in reducing resistance to the therapeutic agent. Examples of such compounds are those which inhibit P-glycoprotein or other cell mechanisms which are involved in excluding intracellular accumulation of drugs.

The formulation may also contain carriers, diluents and excipients. Details of pharmaceutically acceptable carriers, diluents and excipients and methods of preparing pharmaceutical compositions and formulations are provided in Remmingtons *Pharmaceutical Sciences* 18$^{th}$ Edition, 1990, Mack Publishing Co., Easton, Pa., USA.

The active agents for use in the present invention may also be presented for use in veterinary compositions. These may be prepared by any suitable means known in the art. Examples of such compositions include those adapted for:

(a) oral administration, e.g. drenches including aqueous and non-aqueous solutions or suspensions, tablets, boluses, powders, granules, pellets for admixture with feedstuffs, pastes for application to the tongue;

(b) parenteral administration, e.g. subcutaneous, intramuscular or intravenous injection as a sterile solution or suspension or through intra-nasal administration;

(c) topical application, e.g. creams, ointments, gels, lotions, etc.

In a particularly preferred embodiment of the present invention the active agents are administered orally, preferably in the form of a tablet, capsule, lozenge or liquid. The administered composition will preferably include a surfactant and/or solubility improver. A suitable solubility improver is water-soluble polyethoxylated caster oil and an example of a suitable surfactant is Cremophor EL. Dose ranges suitable for flupirtine or pharmaceutical salts, derivatives, homologs or analogs thereof are for example 100 to 1500 mg orally, every six hours including 100, 200, 300, 400, 500, 600, 700, 800, 900, 1000, 1100, 1200, 1300, 1400, 1500. Suitable dose ranges for morphine are 2.5 to 20 mg every 3 to 6 hours such as 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20 and for oxycodone and other opioids 2 to 50 mg every 3 to 12 hours such as 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50.

In combination with flupirtine, the dosage intervals are preferably from about 12 to 24 hours.

The present invention further provides mechanical devices for introduction to or in a body or body cavity coated with a sustained or slow release formulation of flupirtine or a pharmaceutically acceptable salt, derivative, homolog or analog thereof. Optionally, an opioid alone or with other active agents is also included. Examples of mechanical devices include stents, catheters, artificial limbs, pins, needles and the like.

Stents, for example, typically have a lumen, inner and outer surfaces, and openings extending from the outer surface to the inner surface. The present invention extends to a method for coating a surface of a stent. At least a portion of the stent is placed in contact with a coating solution containing a coating material to be deposited on the surface of the stent. A thread is inserted through the lumen of the stent, and relative motion between the stent and the thread is produced to substantially remove coating material within the openings.

The thread can have a diameter substantially smaller than the diameter of the lumen. The thread can be inserted through the lumen either after or prior to contacting the stent with the coating solution. Relative motion between the stent and the thread can be produced prior to contacting the stent with the coating solution to clean the stent. The thread can be either a filament or a cable with a plurality of wires. The thread can be made of a metallic or polymeric material.

The stent can be dipped into the coating solution or spray coated with the coating solution. The coating material can include a biocompatible polymer, either with or without a pharmaceutically active compound.

In one embodiment, the relative motion is oscillatory motion produced by a vibrating device. The oscillations can be changed (magnitude and/or frequency) to vary thickness of the coating solution on the stent. In another embodiment, the relative motion is produced by a shaker table. Regardless of the type of motion, the relative motion can be produced either after or while the stent is in contact with the coating solution.

The relative motion between the stent and the thread can include initially moving the stent in a horizontal direction substantially parallel to the length of the thread and subsequently moving the stent in a vertical direction substantially perpendicular to the length of the thread. The movement in the horizontal direction can be repeated, with pauses between repetitions. The movement in the vertical direction can also be repeated, with the horizontal and vertical movements alternating.

In order to smooth the relative motion, the thread can be coupled to a damping compensator. The damping compensator connects the thread to a vibrating device. In one embodiment, the damping compensator comprises first and second filaments connected to the thread.

The relative motion can be motion of the stent along the thread. For example, a first end of the thread can be attached to a first stand at a first height and a second end of the thread is attached to a second stand at a second height. The relative motion is produced by a gravity gradient, with the first height differing from the second height. Furthermore, the stent can be moved back and forth between the first and second stands by sequentially increasing or decreasing at least one of the first and second heights. In this way, multiple coatings can be applied to the stent.

The relative motion can also be rotation of the stent relative to the thread. A stream of gas can be passed along at least a portion of the surface of the stent to rotate the stent relative to the thread. The rotation can also occur in conjunction with other relative motion between the stent and the thread.

The present invention further provides an implantable medical device having an outer surface covered at least in part by a flupirtine or a pharmaceutically acceptable salts, derivative, homolog or analog and optionally an opioid and/or other active agent, a conformal coating of a hydrophobic elastomeric material incorporating an amount of active material therein for timed delivery therefrom and means associated with the conformal coating to provide a non-thrombogenic surface after the timed delivery of the active material.

Preferably, the conformal coating comprises an amount of finely divided biologically active material in the hydrophobic elastomeric material.

The present invention will now be further described with reference to the following examples, which are intended for the purpose of illustration only and are not intended to limit the generality of the subject invention as hereinbefore described.

EXAMPLES

One of the experimental parameters considered in the Examples is the ability to avoid side effects such as sedative effects of morphine or its homology, when used in combination with flupirtine.

The sedative effects of drug combinations were studied using the rotarod test (Example 1). This test assesses the ability of rats to walk on a rotating drum. Doses of drugs and combinations of those drugs that cause no decrement in this ability were in this manner identified. The identified non-sedative doses of drugs used singly and in combination were then tested for antinociceptive effects in models of pain, where the following nociceptive paradigms were adopted:

(a) the electrical current threshold test (Example 2);
(b) carrageenan-induced paw inflammation (Example 3); and
(c) streptozotocin-induced diabetic neuropathy (Example 4).

All experiments reported in Examples 1 through 4 were performed on male Wistar rats (weight 150-200 g for Examples 1 to 3 and weight 65-80 g for Example 4) in an observer-blinded fashion with parallel saline vehicle controls and all drug solutions and vehicle were given intraperitoneally (ip) in a volume of 1.0 ml.

Example 1

Rotarod Test

The rats were naïve to the drugs with no previous exposure to the rotarod test. They were placed on the rotarod accelerator treadmill (7650 accelerator rotarod, Ugo Basile, Italy) set at the minimum speed for two training sessions of 1-2 minutes separated by an interval of 30-60 minutes. After this conditioning period the ip injection of vehicle, drug, or drug combination was given. Five minutes later the animals were placed onto the rotarod at a constant speed of 4 revolutions per minute. As the animal took grip of the drum the accelerator mode was selected on the treadmill, i.e. the rotation rate of the drum was increased linearly at the rate of 20 revolutions per minute every minute thereafter. The time was measured from the start of the acceleration period until the rat fell off the drum; this was the control (pre-treatment) performance time for each rat. A cut-off or maximum run time for the test was 2 minutes because normal non-sedated rats all ran for 2 minutes at which time the test was terminated. This test was performed on each rat for 30 minutes at intervals of 10 minutes between each run. The shortest run time measured after drug injection was identified during the 30-minute test period for each rat. These values were combined for each drug at each dose to calculate means±SEM. The data from saline treated vehicle controls were compared with the data following drug injections using one-way ANOVA with Tukey Kramer post hoc test. These comparisons allowed definition of drug doses that caused sedation.

Groups of rats were tested with the rotarod as above with the following treatments:

(a) Saline
(b) Morphine at doses of 0.4, 0.8, 1.6, 3.2, and 6.4 mg/kg
(c) Flupirtine at doses of 5, 10 and 20 mg/kg (d) A combination of flupirtine at 5 mg/kg with morphine at 0.4 mg/kg (e) A combination of flupirtine at 10 mg/kg with morphine at 1.6 mg/kg Table 1 shows the results of those experiments.

TABLE 1

| | Lowest run time (s) | | |
|---|---|---|---|
| Treatment | n | mean | SD |
| saline control | 30 | 119.2 | 2.8 |
| flupirtine 5 mg/kg ip alone | 18 | 118.4 | 6.1 |
| flupirtine 10 mg/kg ip alone | 20 | 107.7 | 36.7 |
| flupirtine 20 mg/kg ip alone* | 10 | 58.1* | 54.5 |
| morphine 0.4 mg/kg ip alone | 10 | 120 | 0 |
| morphine 0.8 mg/kg ip alone | 10 | 120 | 0 |
| morphine 1.6 mg/kg ip alone | 10 | 110.4 | 19 |
| morphine 3.2 mg/kg ip alone | 10 | 99.6 | 41.7 |
| morphine 6.4 mg/kg ip alone* | 10 | 60* | 41.7 |
| flupirtine 5.0 mg/kg + morphine 0.4 mg/kg together ip | 10 | 119.5 | 1.3 |
| flupirtine 10 mg/kg + morphine 1.6 mg/kg together ip | 10 | 117 | 4.45 | one way Anova + Tukey-Kramer post-hoc test: compared with saline control $*p < 0.05$ It can be concluded from these experiments that sedation is caused by doses of flupirtine greater than 10 mg/kg and morphine greater than 3.2 mg/kg.

Example 2

Carrageenan Paw Inflammation and Paw Flick Test of Nociception

Experimental inflammation of the right hind paw was induced by an intraplantar injection of carrageenan (Sigma-Aldrich Pty. Ltd. Australia; 100 µl of a 2% wt carrageenan solution in saline). Time was allowed for the induction of inflammation. Paw withdrawal latencies were measured using an infrared beam focussed onto the plantar surface of the right hind paw in freely moving animals using apparatus from Ugo Basile.

Paw withdrawal latencies were measured before the induction of inflammation with carrageenan injections until 3 stable readings were obtained (−20, −10 and 0, as shown in Table 2 and FIG. 1). Once inflammation was established, paw thresholds were measured 60, 110 and 120 minutes after the carrageenan injection to confirm the development of hyperalgesia; a decrease in paw withdrawal latency typically from control pre-carrageenan level of 12 seconds down to 6 seconds. A test drug or drug combination was injected and paw pressure values were measured at 10-minute intervals for the following 40 minutes. Replicate values of paw withdrawal times for time of measurement and drug treatment were combined to calculate mean±SEM.

The following drug treatments were given to separate groups of rats:
  Saline controls
  Flupirtine at doses of 5 and 10 mg/kg alone
  Morphine at doses of 0.4, 0.8 and 1.6 mg/kg alone
  Combinations of flupirtine at 5 and 10 mg/kg with morphine at 0.4 mg/kg Time response curves were plotted to determine peak drug effect as shown in FIG. 1.

It can be seen that the effect of the ip drug injection reaches a plateau from 140 to 160 minutes. The values for all withdrawal latencies in each group were combined for testing times −20, −10 and 0 (pre-treatment) and also for 140, 150 and 160 minute readings (post-treatment). A summary of results with carrageenan-induced paw inflammation are shown in the Table 2.

TABLE 2

| | Pre-treatment | | | Post-treatment | | |
|---|---|---|---|---|---|---|
| Treatment | mean | SD | n | mean | SD | n |
| saline controls | 10.98 | 2.27 | 72 | 6.22 | 2.18 | 72 |
| flupirtine 5 mg/kg ip alone | 10.90 | 2.80 | 30 | 5.82 | 1.70 | 30 |
| flupirtine 10 mg/kg alone | 10.97 | 2.42 | 24 | 5.51 | 2.13 | 24 |
| morphine 0.4 mg/kg ip alone | 12.10 | 2.30 | 36 | 5.76 | 3.10 | 36 |
| morphine 0.8 mg/kg alone | 10.02 | 1.75 | 27 | 4.88 | 1.67 | 27 |
| morphine 1.6 mg/kg alone | 10.30 | 2.48 | 72 | 8.88 | 3.15 | 72 |
| flupirtine 5 mg/kg and morphine 0.4 mg/kg ip together | 11.60 | 2.25 | 72 | 8.75 | 3.31 | 72 |
| flupirtine 10 mg/kg and morphine 0.4 mg/kg ip together | 9.66 | 1.46 | 54 | 10.34 | 4.02 | 54 |

Flupirtine 5 and 10 mg/kg or morphine 0.4 and 0.8 mg/kg alone had no effect on carrageenan-induced hyperalgesia. The combination of flupirtine 5 mg/kg with morphine 0.4 mg/kg caused significant reversal of carrageenan-induced hyperalgesia and this was equal to the effect of 1.6 mg/kg morphine given alone; flupirtine increased the antinociceptive effect of morphine fourfold. Flupirtine 5 mg/kg in combination with morphine 0.4 mg/kg led to significantly less hyperalgesia compared with saline or either drug alone $*p<0.001$ one way ANOVA with Tukey-Kramer post hoc test. Finally, complete reversal of carrageenan-induced hyperalgesia was caused by 10 mg/kg flupirtine in combination with 0.4 mg/kg morphine i.e., doses of two drugs that were ineffective when given alone caused complete antinociception in this model of neuropathic pain ($p>0.05$ in comparison with pre carrageenan levels (at −20, −10 and 0 mins in graph above)—one way ANOVA with Tukey-Kramer post hoc test). None of these doses or combinations of drugs caused sedation in the rotarod test.

Example 3

Electrical Current Threshold Test

Figure 2:
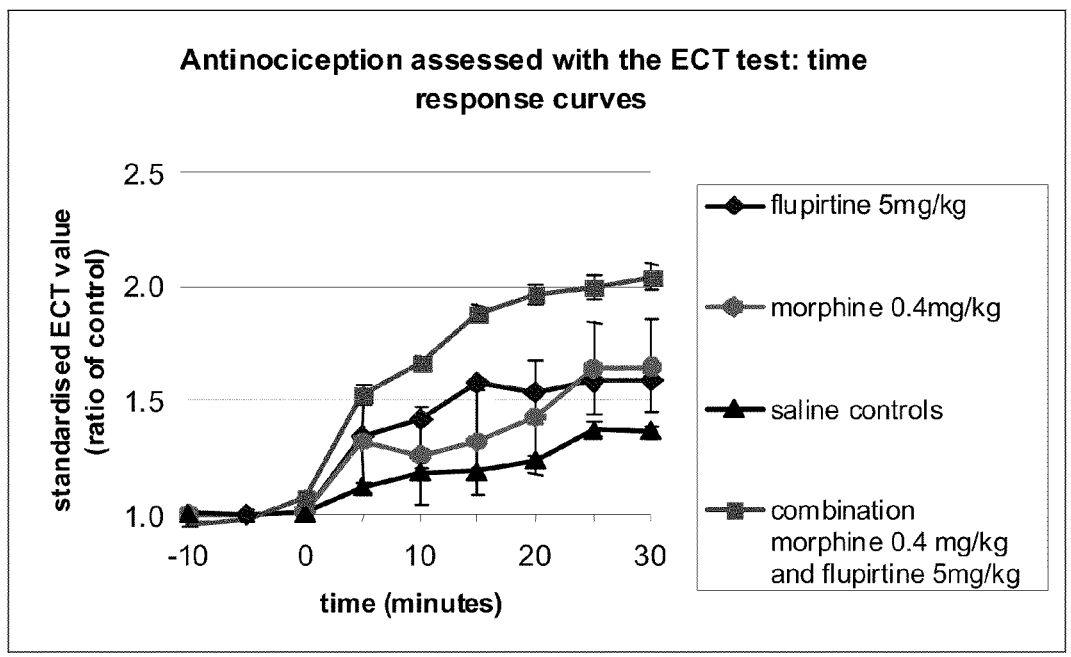
FIG. 2 is a graphical representation of time response curves for antinociception assessed with the Electrical Current Threshold (ECT) test in male Wistar rats, where standardized ECT value as a ratio against the control is plotted against time for saline controls (triangles), flupirtine at 5 mg/kg (diamonds), morphine at 0.4 mg/kg (circles) and the combination of flupirtine at 5 mg/kg with morphine at 0.4 mg/kg (squares)

Rats were placed in a restrainer and two surface electrodes were placed on the tail, 2 and 5 cm from the base. Electrical current (50 Hz, 2 ms pulses, 0-10 mA) was passed through these electrodes to determine the minimum current necessary that caused the rat to squeak of make a strong aversive movement. This value was determined by the "up-down" method ever 5 minutes. Three stable consecutive 5 minute readings were obtained (a, b, and c) followed by an ip injection of drug, drug combination or saline vehicle in an observer blinded fashion. ECT readings were continued every 5 minutes for a further 30 minutes (readings d, e, f, g, h, i). Individual values of ECT measured in mA were standardised to minimise differences between rats due to electrode placement and resistance. This was achieved by dividing all individual readings taken by the mean of the first three pre-drug treatment readings (mean of a+b+c). All values, so transformed, were combined for testing time and drug treatment to calculate means±SEM and plotted as time response curves shown in FIG. 2 for groups of rats that received the following treatments:
  Flupirtine at a dose of 5 mg/kg ip alone
  Flupirtine at a dose of 10 mg/kg ip alone
  Morphine at a dose of 0.4 mg/kg ip alone A combination of morphine at a dose of 0.4 mg/kg with flupirtine at a dose of 5 mg/kg It can be seen from the curves shown in FIG. 2 that drug effects came on and reached a plateau 10-30 minutes after ip injection given after the reading taken at time 0. For statistical comparison all the values for rats in a group were combined for pre-treatment (all a, b and c values) and post-treatment (all e, f, g, h and i values). These are shown in Table 3.

TABLE 3

| SUMMARY DATA ECT PARADIGM | | n rats | n observations | mean | SD |
|---|---|---|---|---|---|
| saline controls | pre | 16 | 48 | 1.00 | 0.05 |
| | post | | 90 | 1.27 | 0.35 |
| flupirtine 5 mg/kg | pre | 20 | 60 | 1.00 | 0.05 |
| | post | | 100 | 1.54 | 0.64 |
| flupirtine 10 mg/kg | pre | 4 | 12 | 1.00 | 0.07 |
| | post | | 20 | 1.92 | 0.79 |
| morphine 0.4 mg/kg | pre | 12 | 36 | 1.00 | 0.06 |
| | post | | 60 | 1.46 | 0.53 |
| combination morphine 0.4 mg/kg and flupirtine 5 mg/kg | pre | 12 | 36 | 1.00 | 0.09 |
| | post | | 60 | 1.91 | 0.89 |

A one way ANOVA with Tukey-Kramer post hoc test was applied to the data in the table above. ECT values after flupirtine 5 or 10 mg/kg, morphine 0.4 mg/kg or the combination of morphine 0.4 mg/kg with flupirtine 5 mg/kg were all significantly greater than saline ($p<0.001$). There was significant antinociception following flupirtine alone at 5 or 10 mg/kg and morphine 0.4 mg/kg ($p<0.001$). The amount of antinociception following morphine 0.4 mg/kg/flupirtine 5 mg/kg combination was significantly greater than morphine 0.4 mg/kg or flupirtine 5 mg/kg given alone ($p<0.001$). It is therefore concluded that non-sedative doses of flupirtine can increase the antinociception following morphine without causing sedation.

Example 4

Streptozotocin-Induced Diabetic Neuropathy

The treatment of neuropathic pain states, including diabetic neuropathy in humans is frequently unsatisfactory. Current pharmacological regimens consist of the tricyclic anti-depressants (Sindrup et al., *Pain,* 42:135-144, 1990; Max, M. B., *Pain,* 42:131-133, 1990; Max, M. B., *Pain,* 50:3-4, 1992), anticonvulsants, systemic local anaesthetics (lignocaine) and mexiletine and, more recently, GABApentin. All have limited success (Arner et al., *Pain,* 33:11-23, 1988; Davis et al., *Pharmacology, Biochemistry and Behavior,* 39:737-742, 1991; Galer, B. S., *Neurology,* 45: Suppl. 9 S17-S25, 1995; Avidan et al., *Israel Journal of Medical Sciences,* 32:331-334, 1996). It is accepted generally that human neuropathic pain states are resistant to opioid treatment (Amer et al. supra). Some researchers have found that opioids may produce antinociceptive effects in neuropathic pain models but at higher than normal doses that also cause sedation revealed by tests such as open field activity monitoring and the rotarod test. This indicates a shift of the dose-response curve to the right, beyond the normal therapeutic range. (Portenoy et al., Pain. 43(3):273-86, 1990)

Courteix and co-workers have developed a diabetes-induced model for neuropathic pain. They found that induction of experimental insulin-dependent diabetes mellitus in rats caused allodynia and hyperalgesia (Courteix et al., *Pain,* 53:81-88, 1993). They went on to show that intravenous morphine induced a dose-dependent antinociceptive effect at doses twice as high as those in normal rats, using the mechanical nociceptive paw pressure test (Courteix et al., *Pain,* 53 supra). Thus the diabetic model reproduced the experience of diabetic neuropathic pain in humans; it is opioid resistant. The experiments reported here use this model to assess the relative efficacy of flupirtine and morphine given alone and in combinations in causing antinociception assessed with paw pressure measured using the Randall Sellito method.

Male Wistar rats (wt 65-80 g) were used for these experiments. Animals were housed 5 per cage under standard laboratory conditions. Food and water were provided ad libitum. In all the experiments attention was paid to ethical guidelines for the investigation of experimental pain in conscious animals (Zimmerman, M., *Pain,* 16:109-110, 1983). All work was carried out with the permission from the Monash University Standing Committee On Ethics in Animal Experimentation (SCAE NUMBER 96-021).

Induction of Diabetes/Hyperalgesia

Rats were injected intraperitoneally (IP) with streptozotocin (STZ) (150 mg/kg total dose) (Sapphire Bioscience) dissolved in sodium chloride (0.9%). The 150 mg dose was given in two 75 mg/kg injections on consecutive days. Diabetes was confirmed one week after injection of STZ by measurement of tail vein blood glucose levels with Ames Glucofilm test strips and a reflectance colorimeter (Ames Glucometer 3, Bayer Diagnostics). Only animals with final blood glucose levels $\geqq 15$ mM were deemed to be diabetic. The rats were retested for hyperglycaemia once per week to confirm continued high blood glucose readings. Hyperalgesia was assessed using the paw pressure test, previously described by Randall and Selitto. (Randall and Selitto, *Archiv. Inst. Pharmacdynamie,* 111:409, 1957)

Tests took place 5 weeks after the first injection of STZ. Animals that had paw pressure nociceptive thresholds below 30 g (60% of the value in normal weight matched rats) were deemed to have developed hyperalgesia/neuropathic pain and thus used in further experiments.

Nociceptive Tests

Figure 3:
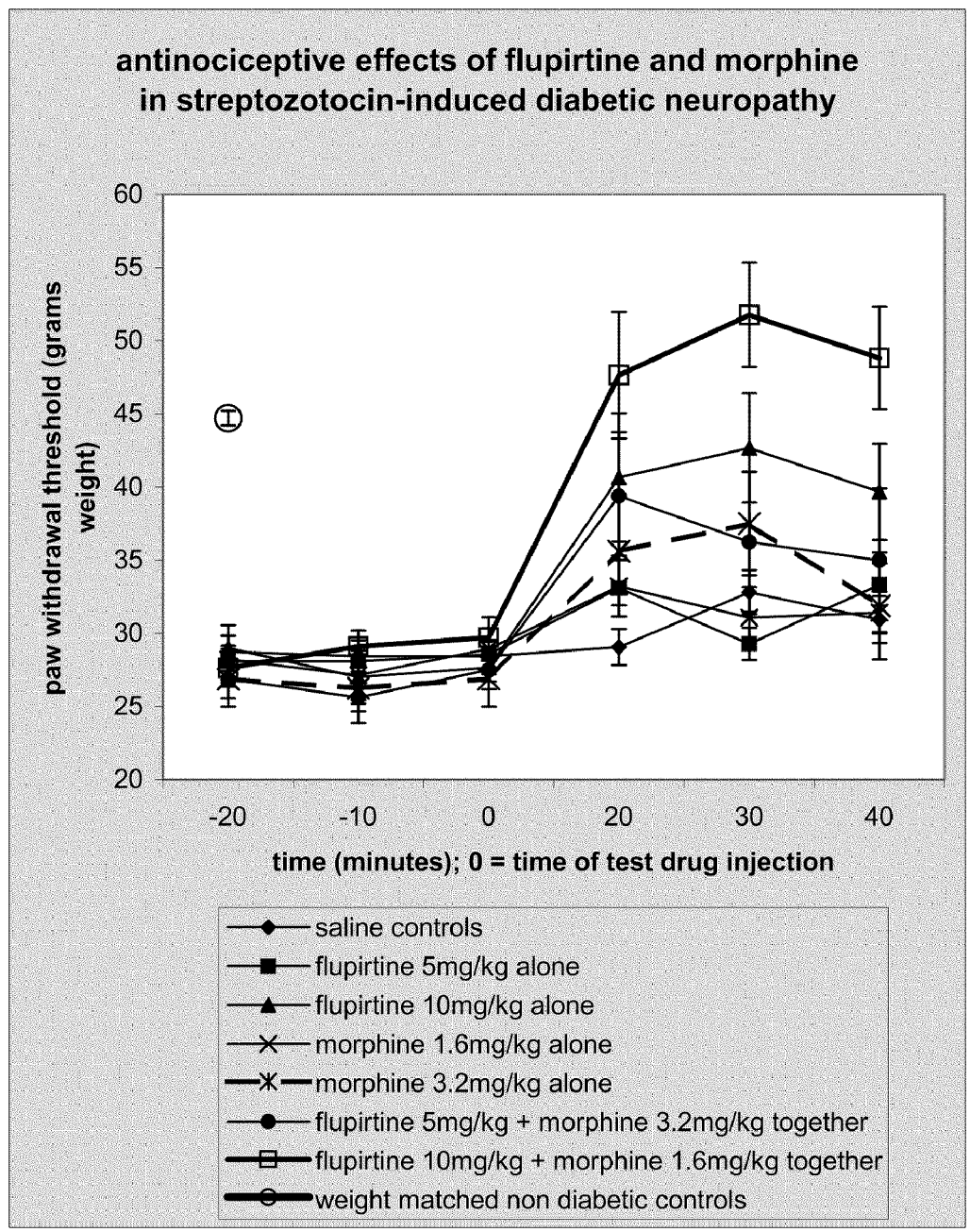
FIG. 3 is a graphical representation of antinociceptive effects in streptozotocin-induced diabetic neuropathy in male Wistar rats, where paw withdrawal threshold (grams) is plotted against time (minutes), where zero time is time of test drug injection, for saline controls (diamonds), flupirtine at 5 mg/kg (squares), flupirtine at 10 mg/kg (triangles), morphine at 1.6 mg/kg (crosses), morphine at 3.2 mg/kg (stars), the combination of flupirtine at 5 mg/kg with morphine at 3.2 mg/kg (closed circles) and the combination of flupirtine at 10 mg/kg with morphine at 1.6 mg/kg (open squares), with results for weight matched non-diabetic controls shown with an open circle.

After the successful documentation of the development of hyperalgesia in diabetic animals by the paw pressure test, more extensive nociceptive testing paradigms were carried out in diabetic neuropathic animals and weight-matched controls; the control rats were 1-2 weeks younger. Paw pressure (PP) was measured by the method described by Randall and Selitto using a Ugo-Basile Algesimeter (Apelex; probe 1 mm; weight: 10 g) (Randall and Selitto, *Archiv. Inst. Pharmacdynamie,* 111 supra; increasing pressure to the left hind paw was applied until vocalization was elicited. Paw withdrawal thresholds were measured in groups of rats 20 minutes and 10 minutes before, immediately before (time 0) and also at 20, 30 and 40 minutes after intraperitoneal (ip) injections of:

saline (controls)
weight matched non diabetic controls (no treatment)
flupirtine 5 mg/kg alone
flupirtine 10 mg/kg alone
morphine 1.6 mg/kg alone
morphine 3.2 mg/kg alone
flupirtine 5 mg/kg plus morphine 3.2 mg/kg together
flupirtine 10 mg/kg plus morphine 1.6 mg/kg together Values in individuals were combined for each testing time to calculate means and SEM which were plotted on time response curves as shown in FIG. 3.

It can be seen that the values of the paw withdrawal thresholds measured at −20, −10 and at 0 were the same for all groups of diabetic rats and these values were significantly below those for normal weight matched controls; diabetes caused hyperalgesia. It can also be seen that the responses to drugs, if present were apparent at 20 minutes after the injection of drug or drug combination and the response was constant and stable between 20 to 40 minutes after the injection which was given at time 0. For each treatment group all the paw withdrawal threshold values taken at time −20, −10 and 0 (pre-drug) were combined as were those taken at time +20, +30, and +40 (post-drug). Means and SD's were calculated for each group for pre- and post-drug administration, as shown in table 4 below. A one-way ANOVA was applied to the values in this table to compare the post drug values with the values for paw withdrawal thresholds in weight-matched non diabetic rats; a return of NS, no significant difference indicates that the drug or drug combination had reversed completely the diabetes-induced hyperalgesia. In addition a one way ANOVA was applied to the data in Table 4 to assess whether any of the drug treatments led to any antinociception i.e., was there a significant increase in paw withdrawal thresholds after the drug treatment compared with the paw withdrawal thresholds before the treatment. A summary of the data relating to diabetic neuropathy as shown in Table 4.

TABLE 4

|  | pre-drug | | | post-drug | | |
|---|---|---|---|---|---|---|
|  | n obs | mean | SD | n obs | mean | SD |
| weight matched non diabetic controls n = 21 rats | 63 | 44.7 | 6.9 | | | |
| saline controls n = 16 rats | 48 | 28.54 | 4.12 | 48 | 30.94 | 5.89 |
| flupirtine 5 mg/kg alone n = 21 rats | 63 | 28.25 | 4.50 | 63 | 31.90 | 7.15 |
| flupirtine 10 mg/kg alone n = 15 rats | 45 | 27.89 | 5.69 | 45 | 41.00 | 14.56 |
| morphine 1.6 mg/kg alone n = 14 rats | 42 | 28.10 | 5.84 | 42 | 31.90 | 6.98 |
| morphine 3.2 mg/kg alone n = 8 rats | 24 | 26.67 | 4.82 | 24 | 35.00 | 10.11 |
| flupirtine 5 mg/kg + morphine 3.2 mg/kg together n = 8 rats | 24 | 26.67 | 4.08 | 24 | 36.88 | 12.84 |
| flupirtine 10 mg/kg + morphine 1.6 mg/kg together n = 17 rats | 51 | 28.82 | 5.16 | 51 | 49.41 | 15.55 |

Complete reversal of streptozotocin-induced diabetic hyperalgesia was caused by flupirtine 10 mg/kg given alone and also flupirtine 10 mg/kg+morphine 1.6 mg/kg together ($p>0.05$); i.e., the paw withdrawal thresholds after the drug treatment were not statistically different from thresholds for normal non-diabetic weight matched controls. Flupirtine 5 mg/kg alone and morphine 1.6 mg/kg alone cause no significant reversal of diabetes-induced hyperalgesia; the paw withdrawal thresholds after the drug injection were not significantly different compared with the thresholds in those rats measured before the drug was injected ($p>0.05$). Morphine 3.2 mg/kg given alone caused significant antinociception; paw thresholds did increase significantly after the drug ($p<0.05$) but those values and the size of that response were significantly less than that caused by a lower dose of morphine (1.6 mg/kg shown to be ineffective when it was given alone) given in combination with flupirtine 10 mg/kg ($p<0.001$). Finally, flupirtine 10 mg/kg in combination with morphine 1.6 mg/kg caused greater antinociception than flupirtine 10 mg/kg alone.

The results reported in Examples 2 through 4 show that non-sedative doses of flupirtine increases the overall antinociceptive effect of morphine without causing sedation in three animal models of pain; electrical, inflammatory and neuropathic. In neuropathic and inflammatory pain models it is possible, using flupirtine in combination with morphine, to cause such significant antinociception as to reverse hyperalgesia such that animals with these pain states are rendered normal with respect to pain sensitivity. This demonstrates utility of flupirtine as an adjunct to opioid analgesics especially in pain states such as inflammatory and neuropathic pain, which are either opioid resistant to the extent that only partial analgesia can be achieved with opioid drugs or are at doses that cause side effects such as sedation. The co-administration of flupirtine with the opioid offers improved pain control in inflammatory and neuropathic pain with doses and combinations that are not accompanied by sedation.

Example 5

Clinical Applications of Flupirtine

The goals of this study
  Perform a pilot study to establish outcomes and variables that might be most useful to evaluate in larger double blind studies
  Show that the administration of flupirtine to cancer patients with neuropathic pain can improve pain experience
  Define the dose
  Quantify the pain reduction along with reduction in the use of other analgesics, including morphine
  Estimate the impact on quality of life
  Show an improvement in side effects and complications of analgesic drug treatments
Methodology, Trial Type and Drug Treatments Involved
  The trial design was an open label dose escalation study carried out on patients with pain associated with cancer that has neuropathic elements as described below. Ethics committee approval and written informed consent from each patient were obtained. All patients referred to the palliative care unit with cancer-related neuropathic pain were considered eligible for entry if they had been receiving opioids for at least 48 hours. The trial lasted eight days. On day 0 the patients were assessed with respect to pain and side effect experiences as well as drug usage. On day 1 there was 24 hours observation and baseline measurements before commencement on flupirtine at a dose of 100 mg four times daily (qid). If the pain was not controlled and there was no evidence of dose limiting side effects as judged by the patient or clinician, the dose could be escalated by 100 mg qid to a maximum of 300 mg qid. Once the patient was pain-free, there was no further dose escalation. Dose increases were only be made if the patient agreed and at the physicians' discretion, taking into account the general clinical situation, pain response, and any toxicity noted. Background "sustained release" and immediate release opioid dosage and other "adjunctive" analgesic drugs were reviewed on a daily basis as is normal practice and they were adjusted in dosage up or down according to clinical need. Patients were encouraged to take their normal opioid and co-analgesics concurrently including any "breakthrough" doses of immediate release morphine mixture.

Patients were assessed daily. Baseline demographic data plus a careful description of the pain were noted at baseline (day 0). On each subsequent occasion, WHO performance status, concomitant medication and any adverse events were noted. Pain was assessed using a linear rating scale based on the Brief Pain Inventory (BPI)-short form, modified for the assessment of nerve pain as described in Daut et al., *Pain;* 17:197-210, 1983 and Galer et al., Neurology; 48:332-338, 1997.

Each patient was asked to categorize their pain and assess it in four ways [average pain; least pain; pain right now; and worst pain in the previous 24 hours] and to score it on a numerical 10 point scale ranging from 1 ("no pain") to 10 ("pain as bad as you can imagine"). They were also be asked to score percentage pain relief (0-100%) and how the pain was affecting their everyday activity on numerical activity scales ranging from 1 ("pain does not interfere") to 10 ("pain completely interferes"). The patients were asked to complete this questionnaire on a daily basis. Patients were also asked specifically about indigestion, change in appetite, drowsiness, nausea, unsteadiness of gait and any other symptoms that develop at each study visit. These "side effects" were scored on a 1 to 4 scale corresponding to "not at all" to "very much".

Case Study 1: Mr JE

JE was a 63 year old, married man diagnosed with cancer of the rectum and anus. He has had progression of the disease into his pelvis and developed liver and pelvic metastases in early 2003. JE had been experiencing intermittent neuropathic pain in his left thigh and buttock for the last two years prior to presentation for a trial of flupirtine. This had been increasing in the two weeks prior to his admission. He described his pain as "a blow torch moving up and down his leg". He also complained of numbness in his left upper thigh. JE subsequently received radiotherapy to this area, and this only provided temporary relief. JE had been prescribed sustained release morphine (Kapanol) 50 mg mane and 100 mg nocte with immediate release morphine mixture (Ordine) 80 mg as required for breakthrough pain. This regimen has been unsuccessful in managing his pain. JE was commenced on an anticonvulsant (sodium valproate-Epilim) and a tricyclic antidepressant (amitryptyline-Endep) 6 days prior to admission and dexamethasone 4 days prior to admission.

Summary of Events During Flupirtine Trial (See Accompanying Table)

Day 0: JE was admitted into the in-patient palliative care facility. His opioid usage for the previous 24 hours was 150 mg Kapanol and 260 mg Ordine together with dexamethasone 4 mg daily plus Epilim 600 mg and Endep 25 mg. His neuropathic pain discriminant function score: was 0.862. This is a function calculated from measurements of twelve different symptoms widely accepted to be indicative of neuropathic pain; a score >0 indicates that the pain is neuropathic (Krause and Backonja. *The Clinical Journal of Pain* 19: 306-314 2003). His average pain score: 7/10, least pain: 4/10 and worst pain: 10/10. WHO performance status was 2 [fully active=0 and the other end of the scale, 4=completely disabled]. At that time, he was experiencing a considerable amount of drowsiness, poor appetite and concentration, and he gait was unsteady. He had lower limb proximal weakness and a global deficit in sensation to pin prick. He felt that the pain was having a significant impact on his life, as he was unable to get around to enjoy time with family and friends.

Day 1: In the 24 hours before commencement on flupirtine JE's opioid usage was 100 mg Kapanol and 310 mg Ordine plus adjuncts: dexamethasone 4 mg; Epilim 600 mg; Endep 25 mg. Neuropathic pain discriminant score: was 2.448, average pain score: 8/10, least pain: 1/10 and worst pain: 10/10. WHO performance status was scored as 3. JE was still experiencing a considerable amount of drowsiness (4), poor appetite (4) and poor concentration (3). He gait was also very unsteady (2) and he had some nausea (2).

Day 2: JE had been taking flupirtine 100 mg QID for 24 hours. Opioid usage for last 24 hours was 150 mg Kapanol with adjuncts: dexamethasone 4 mg; Epilim 600 mg; Endep 25 mg and paracetamol 1 g. His discriminant neuropathic pain score had fallen to a non-neuropathic level: −1.238. The average pain score was 2/10, least pain: 0/10, worst pain: 3/10 and WHO performance status: 3. At this stage JE was still quite drowsy (4) and his colostomy (3) had not functioned since his admission to the palliative care unit. He also developed an occasional intention related myoclonic twitch in his right hand (2). JE's pain had almost completely disappeared and he was enjoying a good appetite and increased ease of movement.

Day 3: JE continued taking flupirtine 100 mg QID. Opioid usage for last 24 hours: 150 mg Kapanol plus adjuncts: dexamethasone 4 mg daily, Epilim 600 mg daily and Endep 25 mg. His neuropathic pain discriminant score had fallen to the minimum level indicating no pain at all: −1.408. His average pain score: 0/10; least pain: 0/10; worst pain: 0/10; and WHO performance status had improved: 2. JE was still quite drowsy (3) and an occasional myoclonic twitch was still present (2). He reported that he was feeling "very well", his appetite had increased and he had no pain at all. The flupirtine dose for the next 24 hours was increased to 200 mg QID and Kapanol reduced by 30 mg/24 hours.

Day 4: JE was taking flupirtine 200 mg QID. Opioid usage for last 24 hours: 120 mg Kapanol with adjuncts: dexamethasone 4 mg daily; Epilim 600 mg daily; Endep 25 mg. His neuropathic pain discriminant score remained at the minimum score of −1.408. Average pain score: 0/10; least pain: 0/10; worst pain: 0/10 and WHO performance status: 3. However there were increased side effects. JE was no longer able to self-care, due to increased sedation (4). He said that he was "feeling weak and tired". The myoclonic twitch was now present at rest and affected both hands and feet (3). He was unable to walk unaided (4) and was having problems staying awake to concentrate (2). JE's colostomy was also yet to function (2). However, he had not experienced any fullness and his appetite remained good. The flupirtine dose was reduced to 100 mg QID and the Kapanol to 80 mg/24 hours.

Day 5: JE continued to take flupirtine 100 mg QID. Opioid usage for last 24 hours: 80 mg Kapanol and adjuncts: dexamethasone 4 mg daily; Epilim 600 mg daily and Endep 25 mg. The neuropathic pain discriminant score remained at the minimum score of −1.408. The average pain score: 0/10; least pain: 0/10; worst pain: 6/10 and WHO performance status deteriorated: 4. JE had an accidental fall in the early hours of the morning whilst trying to make his way to the toilet. He remained confined to bed, because he was unable to walk without assistance. JE was extremely drowsy (4), unable to concentrate (4), had no appetite (4), his colostomy had not functioned (4) and the myoclonic twitch remained (4). The Kapanol dose was reduced further to 40 mg, and the dexamethasone dose was reduced to 2 mg and the Epilim was ceased because the drowsiness and other symptoms were thought to be due to those medicines.

Day 6: The flupirtine dose remained at 100 mg QID. Opioid usage for last 24 hours: 40 mg Kapanol and adjuncts: dexamethasone 2 mg plus Endep 25 mg only. His neuropathic pain discriminant score: −1.048, average pain score: 8/10, least pain: 0/10, worst pain: 9/10 and WHO performance status: 3. JE was less sedated at the time of assessment (3), and he was able to concentrate for longer periods (2). He remained unsteady in his gait (3) but was able to attend to his activities of daily living with minimal assistance. His appetite was returning (2) and the myoclonic twitch was slowly resolving (2).

Day 7: JE continued to take flupirtine at the dose of 100 mg QID. Opioid usage for last 24 hours: 40 mg Kapanol with adjuncts: dexamethasone 2 mg and Endep 25 mg. His neuropathic pain discriminant score had returned to the minimum score of −1.408. His average pain score: 0/10; least pain: 0/10; worst pain: 4/10; and WHO performance status: 3. JE was still experiencing some drowsiness (3) and the myoclonic twitch (2). However, he was able to concentrate for longer periods and remained free from neuropathic pain symptoms.

His appetite remained poor (3). However, his colostomy was functioning regularly. JE had also complained of spider hallucinations (2), not worried by them, as he was aware that they were not really there. He had a similar experience while on morphine in the past. The Endep and Kapanol were ceased and Oxycontin 20 mg BD commenced to address this problem.

Day 8: JE continued to take flupirtine 100 mg QID. Opioid usage for the previous 24 hours: 40 mg Oxycontin (sustained release oxycodone)+5 mg Endone (immediate release oxycodone). Oxycodone is approximately twice as potent as morphine and thus JE was taking opioid at a dose equivalent to 90 mg morphine. He also took dexamethasone 2 mg. The neuropathic pain discriminant score was 0.677 with average pain score for the previous 24 hours: 7/10; least pain: 0/10; worst pain: 9/10 and WHO performance status: 3. JE had a numb left foot overnight that kept him awake. He was otherwise feeling well. He was no longer drowsy; the myoclonic twitch has disappeared, as had the hallucinations. He did however remain a little unsteady in his gait (2).

Summary of Events after Flupirtine Trial

On the following day JE was discharged home taking flupirtine dose 100 mg QID with Oxycontin 40 mg/24 hrs. His average pain score for the previous 24 hours was 0/10, least pain: 0/10 and worst pain: 0/10 with a WHO performance status score of 2. He had no pain and was ambulating independently with a walking frame.

Day 18: JE at home, taking flupirtine dose 100 mg QID, Oxycontin 20 mg BD. endone 5 mg for breakthrough required 2-3 during the week and dexamethasone 4 mg for a low platelet count. He had no neuropathic pain symptoms. He said that he was "feeling well, eating everything and getting out and about. JE was still active at the last follow up on day 44 with no neuropathic pain symptoms taking Oxycontin 20 mg bd with no breakthroughs and leading an active life.

To determine the Mean Equivalent Daily Dose (MEDD), the dose and route of each of the opioids the patient has received over the last 24 hours is translated to parenteral morphine equivalent using a standard conversion table (See Table 5). The total MEDD in mgs is measured each day after assessing the patient.

TABLE 5

MEAN EQUIVALENT DAILY DOSE (MEDD) CONVERSION TABLE

| Medication | Route | MEDD_Factor |
|---|---|---|
| Codeine | IM | 0.1 |
| Codeine | O | 0.05 |
| Codeine | PO | 0.05 |
| Codeine | R | 0.05 |
| Codeine | SC | 0.1 |
| Meperidine | IM | 0.1 |
| Meperidine | IV | 0.1 |
| Meperidine | O | 0.05 |
| Meperidine | PO | 0.05 |
| Meperidine | SC | 0.1 |
| Diamorphine | PO | 0.65 |
| Diamorphine | SC | 1.3 |
| Fentanyl | PO | 0.05 |
| Fentanyl | SL | 0.05 |
| Fentanyl | IV | 0.1 |
| Fentanyl | SC | 0.1 |
| Fentanyl | TD | 0.1 |
| Hydromophone | IM | 5 |
| Hydromophone | IV | 5 |
| Hydromophone | O | 2 |
| Hydromophone | PO | 2 |
| Hydromophone | SC | 5 |
| Levo-Dromorani | SC | 5 |
| Methadone | EP | 8 |
| Methadone | IV | 8 |
| Methadone | O | 4 |
| Methadone | PO | 4 |
| Methadone | R | 4 |
| Methadone | SC | 8 |
| Morphine | EP | 1 |
| Morphine | IM | 1 |
| Morphine | IV | 1 |
| Morphine | O | 0.4 |
| Morphine | PO | 0.4 |
| Morphine | R | 0.4 |
| Morphine | SC | 1 |
| Oxycodone | PO | 0.833 |
| Oxycodone | SC | 1.5 |
| Propoxyphene | IM | 0.167 |
| Propoxyphene | IV | 0.167 |
| Propoxyphene | PO | 0.08 |
| Propoxyphene | R | 0.08 |
| Propoxyphene | SC | 0.167 |
| Propoxyphene | TD | 0.167 |

Note:
1. Adjusted dose for Duragesic and Fentanyl when route = "TD" and dose <= 200: Dose × 24
2. MEDD calculation: [DOSE] × [MEDD_Factor]
3. Sufentanil MEDD factors: SC/IV = 1 PO/SL = 0.5

Table 6 summarises the measurements in this case study. Table 6 is split over two pages.

TABLE 6

| OBSERVATIONS | DAY OF OBSERVATION | | | | | | | | |
|---|---|---|---|---|---|---|---|---|---|
| | DAY 0 | DAY 1 | DAY 2 | DAY 3 | DAY 4 | DAY 5 | DAY 6 | DAY 7 | DAY 8 |
| flupirtine dose in last 24 hours | 0 mg | 0 mg | 100 mg qid | 100 mg qid | 200 mg qid | 100 mg qid | 100 mg qid | 100 mg qid | 100 mg qid |
| dose in last 24 hrs: Kapanol-sustained release morphine | 150 mg | 100 mg | 150 mg | 150 mg | 120 mg | 80 mg | 40 mg | 40 mg | 0 mg |
| dose in last 24 hrs: morphine mixture | 260 mg | 310 mg | 0 mg | 0 mg | 0 mg | 0 mg | 0 mg | 0 mg | 0 mg |
| dose in last 24 hours: oxycontin - sustained release oxycodone | 0 mg | 0 mg | 0 mg | 0 mg | 0 mg | 0 mg | 0 mg | 0 mg | 40 mg |
| dose in last 24 hours: oxycodone | 0 mg | 0 mg | 0 mg | 0 mg | 0 mg | 0 mg | 0 mg | 0 mg | 5 mg |
| parental morphine equivalent dose of all opioids added up | 164 mg | 164 mg | 60 mg | 60 mg | 48 mg | 32 mg | 16 mg | 16 mg | 37 mg* |

TABLE 6-continued

| OBSERVATIONS | DAY 0 | DAY 1 | DAY 2 | DAY 3 | DAY 4 | DAY 5 | DAY 6 | DAY 7 | DAY 8 |
|---|---|---|---|---|---|---|---|---|---|
| dose in last 24 hrs: dexamethasone | 8 mg | 4 mg | 4 mg | 4 mg | 4 mg | 4 mg | 2 mg | 2 mg | 2 mg* |
| dose in last 24 hrs: amitryptiline | 25 mg | 25 mg | 25 mg | 25 mg | 25 mg | 25 mg | 25 mg | 25 mg | 0 mg* |
| dose in last 24 hrs: sodium valproate | 600 mg | 600 mg | 600 mg | 600 mg | 600 mg | 600 mg | 600 mg | 600 mg | 0 mg* |
| dose in last 24 hrs: metoclopramide, antiemetic | 0 mg | 0 mg | 0 mg | 0 mg | 0 mg | 0 mg | 0 mg | 0 mg | 0 mg |
| WHO PERFORMANCE STATUS | 2 | 3 | 3 | 2 | 3 | 4 | 3 | 3 | 3 |
| neuropathic dwascriminant function score calculated from: | 0.862 | 2.448 | −1.238 | −1.408 | −1.408 | −1.408 | −1.048 | −1.408 | 0.677* |
| burning pain score | 100 | 90 | 20 | 0 | 0 | 0 | 0 | 0 | 0 |
| score for overly sensitive to touch | 0 | 95 | 0 | 0 | 0 | 0 | 0 | 0 | 0 |
| for shooting pain score | 90 | 95 | 10 | 0 | 0 | 0 | 0 | 0 | 0 |
| numbness score | 60 | 95 | 0 | 0 | 0 | 0 | 0 | 0 | 90 |
| electric pain score | 0 | 95 | 0 | 0 | 0 | 0 | 0 | 0 | 0 |
| tingling pain score | 0 | 95 | 0 | 0 | 0 | 0 | 0 | 0 | 0 |
| squeezing pain score | 70 | 0 | 0 | 0 | 0 | 0 | 0 | 0 | 0 |
| freezing pain score | 0 | 0 | 0 | 0 | 0 | 0 | 0 | 0 | 0 |
| unpleasant pain score | 100 | 95 | 0 | 0 | 0 | 0 | 0 | 0 | 95 |
| overwhelming pain score | 100 | 98 | 0 | 0 | 0 | 0 | 40 | 0 | 95 |
| score for increased pain due to touch | 0 | 0 | 0 | 0 | 0 | 0 | 80 | 0 | 0 |
| score for increased pain due to weather changes | 0 | 0 | 0 | 0 | 0 | 0 | 0 | 0 | 0 |
| AVERAGE PAIN LAST 24 HOURS | 7 | 8 | 2 | 0 | 0 | 0 | 8 | 0 | 7 |
| LEAST PAIN LAST 24 HRS | 4 | 1 | 0 | 0 | 0 | 0 | 0 | 0 | 0* |
| PAIN SCORE RIGHT NOW | 4 | 1 | 0 | 0 | 0 | 0 | 8 | 0 | 9 |
| WORST PAIN SCORE LAST 24 HOURS | 10 | 10 | 2 | 0 | 0 | 6 | 9 | 4 | 9* |
| PERCENTAGE PAIN RELIEF LAST 24 HOURS | N/A | N/A | N/A | N/A | N/A | N/A | N/A | N/A | N/A |
| SCORE GENERAL ACTIVITY | 8 | 5 | 1 | 1 | | 1 | 1 | 1 | 1* |
| SCORE MOOD | 1 | 1 | 1 | 1 | 1 | 1 | 1 | 1 | 8 |
| SCORE WALKING | 8 | 7 | 1 | 1 | 1 | 1 | 1 | 1 | 1* |
| SCORE RELATIONSHIPS | 1 | 1 | 1 | 1 | 1 | 1 | 1 | 1 | 1 |
| SCORE SLEEP | 1 | 3 | 1 | 1 | 1 | 1 | 1 | 1 | 10 |
| SCORE ENJOYMENT | 8 | 8 | 1 | 1 | 1 | 3 | 1 | 1 | 8 |
| SCORE TOTAL ACTIVITY | 8 | 8 | 1 | 1 | 1 | 1 | 1 | 1 | 1* |
| SCORE INDIGESTION | 1 | 1 | 1 | 1 | 1 | 1 | 1 | 1 | 1 |
| SCORE POOR APPETITE | 3 | 4 | 1 | 1 | 1 | 4 | 2 | 3 | 1* |
| SCORE DROWSINESS | 4 | 4 | 4 | 3 | 4 | 4 | 3 | 3 | 1* |
| SCORE NAUSEA | 1 | 2 | 1 | 1 | 1 | 1 | 1 | 1 | 1* |
| SCORE UNSTEADINESS OF GAIT | 4 | 2 | 1 | 1 | 4 | 4 | 3 | 2 | 2* |
| SCORE CONSTIPATION | 2 | 1 | 3 | 1 | 3 | 4 | 1 | 1 | 1* |
| SCORE POOR CONCENTRATION | 3 | 3 | 1 | 1 | 2 | 4 | 2 | 1 | 1* |
| other symptoms | | | | | | | | 2-hallucinations | 1-hallucinations |
| other symptom | | 1 | 2-twitch | 2-twitch | 3-twitch | 4-twitch | 2-twitch | 2-twitch | 1-twitch |

Asterisk (*) indicates an improvement on day X compared to day 1.

Case Study 2: Mr RM

RM was an 80 year old, widowed man diagnosed with metastatic bladder cancer. RM had required in the past surgical fixation of a fractured pelvis following a fall. Ten weeks before this study, RM was found to have a pathological fracture of his left acetabulum, located above his hip prosthesis and multiple pulmonary metastases. Bone scan and CT did not reveal evidence of metastases in RM's sacrum or hip. He was admitted to hospital in because of decreased mobility caused by ongoing pain in his left buttock and leg. He also had a right side foot drop and absent right ankle jerk but he retained normal bilateral sensation and tone in the legs. An MRI showed a solitary metastasis of S2 with no cauda equina or nerve root involvement. RM had been experiencing fairly constant neuropathic type pain in his right buttock and leg since for four months prior to the study. The pain was initially experienced in his left leg and hip and then as time went on, it spread towards and down his right side. On admission for the study, the pain was concentrated down his right side. RM described a "burning" pain that radiated from his hip and down his leg. The pain was always present but it tended to be worst in the mornings. RM had experienced little improvement with analgesics. He had been prescribed sustained release oxycodone 20 mg BD with immediate release Endone 5 mg and hydromorphone 1 mg sc. as required for breakthrough pain. RM was treated with ketamine for six days prior to this trial; it was ceased 24 hours before flupirtine dosing began. The ketamine failed to control pain and neuropathic pain scores increased towards the end of that treatment (see table below comparing day 0 with day 1. In an attempt to control the pain RM was also commenced on a cox-2 inhibitor (Celebrex) and an anticonvulsant (Gabapentin) in the weeks before the flupirtine trial began. This regimen had also been unsuccessful in managing his pain.

Summary of Events During Flupirtine Trial

Day 0: RM was admitted into the in-patient palliative care facility. His opioid usage for the previous 24 hours was 40 mg oxycodone orally and 1.5 mg hydromorphone subcutaneously together with Gabapentin 100 mg daily, Celebrex 400 mg and strict 6 hourly Paracetamol. In spite of this treatment he still had significant neuropathic pain; his neuropathic pain discriminant function score: was 0.077. This is a function calculated from measurements of twelve different symptoms widely accepted to be indicative of neuropathic pain; a score >0 indicates that the pain is neuropathic (Development of a Neuropathic Pain Questionnaire. Krause and Backonja, *The Clinical Journal of Pain* 19: 306-314, 2003). His average pain score: 5/10, least pain: 0/10 and worst pain: 10/10. WHO performance status was 3 [fully active=0 and the other end of the scale, 4=completely disabled]. At that time he was experiencing a considerable amount of constipation, poor appetite and unsteady gait (walks with the aid of a wheelie frame). He felt that the pain was having a significant impact on his life, as it seemed the pain was always present.

Day 1: In the 24 hours before commencement on flupirtine RM's opioid usage was: 40 mg oxycodone orally, 15 mg Endone orally and 0.5 mg hydromorphone subcutaneously plus adjuncts: Gabapentin 100 mg daily, Celebrex 400 mg and strict 6 hourly Paracetamol. RM was receiving ketamine prior to his transfer, a period of $20^+$ hours elapsed before his commencement on flupirtine. Neuropathic pain discriminant score was highly significant at the value of 0.262. His average pain score: 8/10, least pain: 0/10 and worst pain: 10/10. WHO performance status was scored as 3. RM was experiencing poor appetite (4), unsteady gait (4), nausea (3) and some drowsiness (2).

Day 2: RM had been taking flupirtine 100 mg QID for 24 hours. Opioid usage for last 24 hours: 40 mg oxycodone orally and 2.5 mg hydromorphone subcutaneously with adjuncts: Gabapentin 100 mg daily, Celebrex 400 mg and strict 6 hourly Paracetamol. Neuropathic pain discriminant score had fallen dramatically to a non-neuropathic level: −0.228. The average pain score had also fallen to 5/10, least pain: 0/10, worst pain: 8/10 and WHO performance status: 3. RM's appetite remained poor (3), as did his gait (4). He was also drowsy (3) and found it a little difficult to concentrate (3). RM felt that this "foggy" feeling was due to the Valium he had received at midnight for night-time sedation.

Day 3: RM continued taking flupirtine 100 mg QID. Opioid usage for last 24 hours: 40 mg oxycodone orally and 2 mg hydromorphone subcutaneously plus adjuncts: Gabapentin 100 mg daily, Celebrex 400 mg and strict 6 hourly Paracetamol. Neuropathic pain discriminant score remained at a low non-neuropathic level: −1.008. His average pain score: 8/10; least pain: 0/10; worst pain: 8/10; and WHO performance status: 3. RM was less drowsy (2) and remained unsteady on his feet (4). RM reported that his sleeping had improved, as had his appetite.

Day 4: RM continued to take flupirtine 100 mg QID. Opioid usage for last 24 hours: 40 mg oxycodone and 5 mg Endone both orally, no hydromorphone breakthrough injections, with adjuncts: Gabapentin 100 mg daily, Celebrex 400 mg and strict 6 hourly Paracetamol. Neuropathic pain discriminant score remained low and at a non-neuropathic level: −1.138. Average pain score: 8/10; least pain: 0/10; worst pain: 8/10 and WHO performance status: 3. RM feels that his pain relief had improved, it now feels "like a bruise". RM had a short bout of nausea (2) in the morning that was treated with maxalon 10 mg. He was also quite constipated (3); a state normal for him and for which he normally took aperients to assist his bowel. His gait remained unsteady (4); nevertheless he was quite active walking around the unit to the lounge. RM thinks that the pain relief was much better today. He reported that 75% pain relief had been achieved. This compared markedly with the 10% relief he reported on day 1 before treatment with flupirtine.

Day 5: RM continued to take flupirtine 100 mg QID. Opioid usage for last 24 hours: 40 mg oxycodone orally and 1 mg hydromorphone subcutaneously with adjuncts: Gabapentin 100 mg daily, Celebrex 400 mg and strict 6 hourly Paracetamol. Neuropathic pain discriminant score: −1.003. The average pain score: 8/10; least pain: 2/10; worst pain: 9/10 and WHO performance status: 3. RM was experiencing some constipation (2), poor appetite (2), and unsteady gait (4). He was also found it a little difficult to concentrate (2) on the questionnaire with his mind tending to wander. He still reported a high percentage of pain relief.

Day 6: RM continued taking flupirtine 100 mg QID. Opioid usage for last 24 hours: 40 mg oxycodone orally and 3 mg hydromorphone subcutaneously with adjuncts: Gabapentin 100 mg daily, Celebrex 400 mg and strict 6 hourly Paracetamol. Neuropathic pain discriminant score remained low and non-neuropathic: −1.168. This indicated that the pain being experienced was not of neuropathic origin. The average pain score had decreased: 4/10; least pain: 2/10; worst pain: 7/10 and WHO performance status: 3. The neuropathic element to RM's pain appeared to have improved from the first day of taking flupirtine. However he was still experiencing a significant amount of incident pain. Since the reason for addition of flupirtine was to treat the opioid resistant neuropathic pain, the dosage was kept the same but opioid dose was increased, to 30 mg oxycodone orally BD. This follows the concept of this invention of using a combination of opioid with flupirtine in the management of pain states that involve a significant neuropathic pain element that is resistant to the opioid given on its own. He still had some loss of appetite (2), constipation (2), poor concentration (2) and nausea (2). His gait remained unsteady (4).

Day 7: RM continued to take flupirtine 100 mg QID. Opioid usage for last 24 hours: 60 mg oxycodone and 10 mg Endone both orally with adjuncts: Gabapentin 100 mg daily, Celebrex 400 mg and strict 6 hourly Paracetamol. Neuropathic pain discriminant score remained low and non-neuropathic: −1.168. The other pain scores had all fallen: average pain score 3/10; least pain 0/10; worst pain 5/10. WHO performance status remained at 3. RM seemed to be a little flat. He admitted to feeling "a bit down today". He felt that the pain had eased but that he still "wasn't right". RM complained that there was not much to do in the unit and that at times he was bored. He had increased loss of appetite (3), and remained a little constipated (2) and nauseated (2). His gait remained unsteady (4) and he had a little difficulty concentrating (2).

Day 8: RM continued to take flupirtine 100 mg QID. Opioid usage for last 24 hours: 60 mg oxycodone, 5 mg Endone both orally and 2 mg hydromorphone subcutaneously with adjuncts: Gabapentin 100 mg daily, Celebrex 400 mg and strict 6 hourly Paracetamol. Neuropathic pain discriminant score: −1.198. The average pain score: 4/10; least pain: 1/10; worst pain: 7/10 and WHO performance status: 3. RM had experienced two bouts of nausea (3) requiring 10 mg maxalon on both occasions. His appetite (2) and concentration (2) had been poor at times. He was constipated (3) and had received his regular aperients. RM felt that the flupirtine had "been good" even though his pain is still present and wished to remain on his current dose after discharge from the palliative care unit.

Table 7 below summarises the measurements in this case study. Table 7 is split over two pages.

TABLE 7

| OBSERVATIONS | DAY 0 | DAY 1 | DAY 2 | DAY 3 | DAY 4 | DAY 5 | DAY 6 | DAY 7 | DAY 8 |
|---|---|---|---|---|---|---|---|---|---|
| flupirtine dose in last 24 hours | 0 mg | 0 mg | 100 mg qid | 100 mg qid | 100 mg qid | 100 mg qid | 100 mg qid | 100 mg qid | 100 mg qid |
| dose in last 24 hours: oxycontin-sustained release oxycodone | 40 mg | 40 mg | 40 mg | 40 mg | 40 mg | 40 mg | 40 mg | 60 mg | 60 mg |
| dose in last 24 hours: oxycodone | 0 mg | 15 mg | 0 mg | 0 mg | 5 mg | 0 mg | 0 mg | 10 mg | 5 mg |
| dose in last 24 hours: hydromorphone | 1.5 mg | 0.5 mg | 2.5 mg | 2 mg | 0 mg | 1 mg | 3 mg | 0 mg | 2 mg |
| parenteral morphine equivalent dose of all opioids added up | 40.82 | 48.315 | 45.82 | 43.32 | 37.485 | 38.32 | 48.32 | 58.31 | 64.145 |
| dose in last 24 hrs: Celebrex | 400 mg | 400 mg | 400 mg | 400 mg | 400 mg | 400 mg | 400 mg | 400 mg | 400 mg |
| dose in last 24 hrs: gabapentin | 100 mg | 100 mg | 100 mg | 100 mg | 100 mg | 100 mg | 100 mg | 100 mg | 100 mg |
| dose in last 24 hrs: ketamine | 450 mg | 84 mg | 0 mg | 0 mg | 0 mg | 0 mg | 0 mg | 0 mg | 0 mg |
| dose in last 24 hrs: paracetamol | 3G | 3G | 4G | 4G | 4G | 4G | 4G | 4G | 3G |
| dose in last 24 hrs: metoclopramide, antiemetic | 0 mg | 0 mg | 0 mg | 0 mg | 0 mg | 0 mg | 10 mg | 0 mg | 20 mg |
| WHO PERFORMANCE STATUS | 3 | 3 | 3 | 3 | 3 | 3 | 3 | 3 | 3 |
| neuropathic discriminant function score calculated from: | 0.077 | 0.262 | −0.228 | −1.008 | −1.138 | −1.003 | −1.168 | −1.168 | −1.198* |
| burning pain score | 100 | 90 | 70 | 0 | 0 | 0 | 0 | 0 | 0* |
| score for overly sensitive to touch | 50 | 20 | 0 | 0 | 0 | 0 | 0 | 0 | 0* |
| for shooting pain score | 0 | 100 | 80 | 20 | 0 | 0 | 0 | 0 | 0* |
| numbness score | 0 | 0 | 0 | 0 | 0 | 0 | 0 | 0 | 0 |
| electric pain score | 0 | 0 | 0 | 0 | 0 | 0 | 0 | 0 | 0 |
| tingling pain score | 50 | 20 | 0 | 0 | 0 | 0 | 0 | 0 | 0* |
| squeezing pain score | 0 | 0 | 0 | 0 | 0 | 0 | 0 | 0 | 0 |
| freezing pain score | 0 | 0 | 0 | 0 | 0 | 0 | 0 | 0 | 0 |
| unpleasant pain score | 70 | 100 | 95 | 75 | 60 | 80 | 60 | 50 | 45* |
| overwhelming pain score | 95 | 90 | 70 | 50 | 30 | 25 | 40 | 20 | 20* |
| score for increased pain due to touch | 0 | 0 | 0 | 0 | 0 | 0 | 0 | 0 | 0 |
| score for increased pain due to weather changes | 0 | 0 | 0 | 0 | 0 | 0 | 0 | 0 | 0 |
| AVERAGE PAIN LAST 24 HOURS | 5 | 8 | 5 | 8 | 8 | 8 | 4 | 3 | 4* |
| LEAST PAIN LAST 24 HRS | 0 | 0 | 0 | 0 | 0 | 2 | 2 | 0 | 1 |
| PAIN SCORE RIGHT NOW | 5 | 4 | 6 | 8 | 2.5 | 5 | 6 | 5 | 7 |
| WORST PAIN SCORE LAST 24 HOURS | 10 | 10 | 8 | 8 | 8 | 9 | 7 | 5 | 7* |
| PERCENTAGE PAIN RELIEF LAST 24 HOURS | 10 | 10 | 15 | 15 | 75 | 65 | 50 | 75 | 75* |
| SCORE GENERAL ACTIVITY | 8 | 8 | 6 | 5 | 5 | 6 | 6 | 5 | 5* |
| SCORE MOOD | 6 | 4 | 4 | 4 | 2 | 3 | 4 | 6 | 4* |
| SCORE WALKING | 6 | 7 | 6 | 6 | 5 | 5 | 6 | 6 | 6* |
| SCORE RELATIONSHIPS | 3 | 3 | 3 | 3 | 3 | 3 | 3 | 3 | 3 |
| SCORE SLEEP | 2 | 6 | 6 | 1 | 2 | 6 | 4 | 6 | 1* |
| SCORE ENJOYMENT | 6 | 6 | 4 | 4 | 3 | 6 | 6 | 6 | 4* |
| SCORE TOTAL ACTIVITY | 8 | 8 | 6 | 5 | 5 | 6 | 6 | 5 | 5* |
| SCORE INDIGESTION | 1 | 1 | 1 | 1 | 1 | 1 | 1 | 1 | 1 |
| SCORE POOR APPETITE | 4 | 4 | 3 | 1 | 1 | 2 | 2 | 3 | 2* |
| SCORE DROWSINESS | 2 | 2 | 3 | 2 | 1 | 1 | 1 | 1 | 1* |
| SCORE NAUSEA | 2 | 3 | 1 | 1 | 2 | 1 | 2 | 2 | 3 |
| SCORE UNSTEADINESS OF GAIT | 4 | 4 | 4 | 4 | 4 | 4 | 4 | 4 | 4 |
| SCORE CONSTIPATION | 3 | 1 | 1 | 1 | 3 | 2 | 2 | 2 | 3 |
| SCORE POOR CONCENTRATION | 2 | 1 | 3 | 1 | 1 | 2 | 2 | 2 | 2 |

Asterisk (*) indicates an improvement on day X compared to day 1.

Example 6

A Rat Model of Bone Cancer Pain

Sprague-Dawley rats receive intra-tibial injections of syngeneic MRMT-1 rat mammary gland carcinoma cells and develop behavioural signs indicative of pain, including: mechanical allodynia, difference of weight bearing between hind paws and mechanical hyperalgesia. The development of the bone tumour and structural damage to the bone is monitored by radiological analysis, quantitative measurement of mineral content and histology. Intra-tibial injections of $3 \times 10^3$ or $3 \times 10^4$ syngeneic MRMT-1 cells produce a rapidly expanding tumor within the boundaries of the tibia, causing severe remodelling of the bone. Radiographs show extensive damage to the cortical bone and the trabeculae by day 10-14 after inoculation of $3 \times 10^3$ MRMT-1 cells, and by day 20, the damage is threatening the integrity of the tibial bone. While both mineral content and mineral density decrease significantly in the cancerous bone, osteoclast numbers in the peritumoural compact bone remain unchanged. Tartarate-resistant acid phosphatase staining reveals a large number of polykariotic cells, resembling those of osteoclasts within the tumor. No tumor growth is observed after the injection of heat-killed MRMT-1 cells. Intra-tibial injections of $3 \times 10^3$ or $3 \times 10^4$ MRMT-1 cells, heat-killed cells or vehicle do not show changes in body weight and core temperature over 19-20 days. The general activity of animals after injection with live or heat-killed MRMT-1 cells is higher than that of the control group Rats which receive intra-tibial injections of MRMT-1 cells display the gradual development of mechanical allodynia and mechanical hyperalgesia and reduce weight bearing on the affected limb, beginning on day 12-14 or 10-12 following injection of $3\times10^3$ or $3\times10^4$ cells, respectively. These symptoms are not observed in rats receiving heat-killed cells or vehicle. Experimental and control animals are each divided into three groups 1, 2, 3. Wherein animals that were injected with either $3\times10^3$ or $3\times10^4$ syngeneic MRMT-1 cells who were treated with flupirtine and morphine showed, when compared to either control animals or animals treated with saline.

Example 7

Animal Models of Pain

Spinal Cord Injury Models

Central pain models are used to test the analgesic effects of flupirtine both with and without morphine. The majority of central pain models are based on spinal cord injury (SCI). Dysesthesia is one of the major life-style altering changes that SCI patients have to cope with. Both spontaneous and evoked pain are frequent sequelae of traumatic or ischemic SCI.

Neuroma Model

Mice are subjected to complete nerve transection at multiple locations along the sciatic nerve resulting in the development of a neuroma at the proximal nerve stump which consists of regenerative nerve sprouting in all directions. Mice subjected to such surgery typically self attack and mutilate the denervated limb. The mice are then divided into three groups: 1) flupirtine alone; 2) flupirtine and morphine; and 3) saline. The animals are then monitored using standard behavioural tests for pain, such as the paw withdrawal threshold or paw flick latency.

Chronic Constriction Injury Model (CCI or Bennett Model)

Rat have loose ties on the sciatic nerve (left or right side) with four chromic gut ligatures at the mid-thigh level. These rats exhibit behavioural signs of spontaneous pain such as mild to moderate autotomy, guarding, excessive licking and limping of ipslateral hind paw, and avoidance of placing weight on the injury side. Hyperalgesia due to noxious thermal and mechanical stimuli is detectable, as are cold allodynia and tactile allodynia. All pain signs last for the entire duration of the study (over 2 months). The rats are then divided into three groups: 1) flupirtine alone; 2) flupirtine and morphine; and 3) saline. The animals are then monitored using standard behavioural tests for pain, such as the paw withdrawal threshold or paw flick latency.

Partial Sciatic Nerve Ligation Model (PSL or Seltzer Model)

Rats are subjected to ligation of the ipsilateral sciatic nerve at he high thigh level, so that $\frac{1}{3}$-$\frac{1}{2}$ thickness of the sciatic nerve is trapped in the ligature. Such rats exhibit signs of allodynia to von Frey hair stimulation and hyperalgesia to both thermal and mechno-noxious stimuli with hours of ligation; the symptoms last for over 7 months. Ligated rats also display signs of spontaneous pain in the forms of paw guarding and licking on the injury side. The evoked pain can develop into bilateral patterns. The rats are then divided into three groups: 1) flupirtine alone; 2) flupirtine and morphine; and 3) saline. The animals are then monitored using standard behavioural tests for pain, such as the paw withdrawal threshold or paw flick latency.

L5/L6 Spinal Nerve Ligation Model (SNL)

In this model the mice are subjected to unilateral and tight ligation of the L5 and L6 spinal nerve at a location distal to the dorsal route ganglia. Allodynia and hyperalgesia develop quickly after ligation, and last for at least 4 months. Although there are behavioral signs of spontaneous pain (guarding, licking, and lifting of ipsilateral hind paw), autotomy is absent in the SNL. The mice are then divided into three groups: 1) flupirtine alone; 2) flupirtine and morphine; and 3) saline. The animals are then monitored using standard behavioural tests for pain, such as the paw withdrawal threshold or paw flick latency.

L5 Spinal Nerve Ligation

Rats are subjected to L5 ligation and exhibit long lasting hyperalgesia and mechanical allodynia. The rats are then divided into three groups: 1) flupirtine alone; 2) flupirtine and morphine; and 3) saline. The animals are then monitored using standard behavioural tests for pain, such as the paw withdrawal threshold or paw flick latency.

Sciatic Cryoneurolysis Model (SCN)

Rats are subjected to freezing of the sciatic nerve to produce nerve injury in this model. SCN induces autotomy and touch allodynia which lasts 15 to 21 days. The rats are then divided into three groups: 1) flupirtine alone; 2) flupirtine and morphine; and 3) saline. The animals are then monitored using standard behavioural tests for pain, such as the paw withdrawal threshold or paw flick latency.

Inferior Caudal Trunk Resection Model

Rats are subjected to unilateral resection of the inferior caudal trunk between S3 and S4 nerves. Mechanical allodynia and cold or thermal hyperalgesia develop within a day after injury, and can last for weeks. The rats are then divided into three groups: 1) flupirtine alone; 2) flupirtine and morphine; and 3) saline. The animals are then monitored using standard behavioural tests for pain, such as the paw withdrawal threshold or paw flick latency.

Sciatic Inflammatory Neuritis Model (SIN)

Rats are injected with zymosan around the sciatic nerve. In this model allodynia is seen hours after the injection. The rats are then divided into three groups: 1) flupirtine alone; 2) flupirtine and morphine; and 3) saline. The animals are then monitored using standard behavioural tests for pain, such as the paw withdrawal threshold or paw flick latency.

Cancer Pain Models

Cancer-related pain may be caused by tumor infiltration or compression of nerve, plexus, or roots, immunoreactive and pronociceptive substances released from tumors, or by treatment (chemotherapy, radiation, or surgery).

Chemotherapy-Induced Peripheral Neuropathy Models

Rats are injected with either vinca alkaloids, platinum compounds or Taxols or other chemotherapeutic agents also capable of inducing neuropathy. The rats are then divided into three groups: 1) flupirtine alone; 2) flupirtine and morphine; and 3) saline. The animals are then monitored using standard behavioural tests for pain, such as the paw withdrawal threshold or paw flick latency.

Vincristine-Induced Peripheral Neuropathy Model (VIPN)

Rats are injected daily with vincristine for 10 days (5 consecutive drugs days+2 drug-free days+5 more drug days) resulting in the production of hyperalgesia. The rats are then divided into three groups: 1) flupirtine alone; 2) flupirtine and morphine; and 3) saline. The animals are then monitored using standard behavioural tests for pain, such as the paw withdrawal threshold or paw flick latency.

Alternatively, rats are subjected to a continuous intravenous vincristine infusion so as to induce in a dose-dependent tactile allodynia. The rats are then divided into three groups: 1) flupirtine alone; 2) flupirtine and morphine; and 3) saline. The animals are then monitored using standard behavioural tests for pain, such as the paw withdrawal threshold or paw flick latency.

Taxol-Induced Peripheral Neuropathy Model (TIPN)

Paclitaxel (Taxol) is an antineoplastic agent derived from the Pacific yew tree Taxus brevifolia and is used to treat a variety of cancers, including ovarian and breast tumors, and non-small cell lung cancer. Taxol binds to tubulin (at a site different from that used by the vinca alkaloids) and blocks polymerization of microtubules. Its effectiveness is limited by the development of severe painful peripheral neuropathy that is dose-dependent. The incidence of Taxol neuropathy is estimated to be 50-90%, and is characterised by dysesthesia (e.g. numbness, tingling and burning pain) of the hands and feet. Rats are injected with Taxol resulting in neuropathic pain. The rats are then divided into three groups: 1) flupirtine alone; 2) flupirtine and morphine; and 3) saline. The animals are then monitored using standard behavioural tests for pain, such as the paw withdrawal threshold or paw flick latency.

Cisplatin-Induced Peripheral Neuropathy (CIPN)

Cisplatin is used to treat ovarian and small cell lung cancer. Cisplatin induces polyneuropathy that is dose- and treatment duration-dependent, and can last for over 10 years. Rats are subjected to repeated daily injections (i.p.) of cisplatin which produces mechanical allodynia and hyperalgesia. The rats are then divided into three groups: 1) flupirtine alone; 2) flupirtine and morphine; and 3) saline. The animals are then monitored using standard behavioural tests for pain, such as the paw withdrawal threshold or paw flick latency.

Cancer Invasion Pain Model (CIP)

Peripheral nerve injury and neuritis models can be used to stimulate peripheral nerve damage due to cancer invasion. Meth A sarcoma cells are implanted around the sciatic in BALB/c mice. There animals develop signs of grows and compresses the nerve. Signs of spontaneous pain (paw lifting) are also visible. The rats are then divided into three groups: 1) flupirtine alone; 2) flupirtine and morphine; and 3) saline. The animals are then monitored using standard behavioural tests for pain, such as the paw withdrawal threshold or paw flick latency.

Bone Cancer Pain Models

Bone cancer pain is one of the most common cancer-related pains. Bone cancer can be primary or metastatic from breast, prostate, ovary and lung tumors. Deep pain with a burning and stabbing sensation is often described by bone cancer patients.

Mouse Femur Bone Cancer Pain Model

Osteolytic mouse sarcoma NCTC2472 cells are injected into the marrow space of the femur bone to induce bone cancer. For histocompatibility, C3H/HeJ mice are used for this model. Within 5 days of sarcoma injection, cancer-induced bone destruction and osteoclastogenesis begin. Signs of spontaneous (nocifensive behaviour, spontaneous flinching) and evoked pain (palpation-evoked flinching), as well as changes in neurochemical markers occur within 14 days, and can be attenuated by osteoprotegerin. The mice are then divided into three groups: 1) flupirtine alone; 2) flupirtine and morphine; and 3) saline. The animals are then monitored using standard behavioural tests for pain, such as the paw withdrawal threshold or paw flick latency.

Mouse Calcaneus Bone Cancer Pain (CBC)

NCTC2472 cells are injected into mouse calcaneus bone. Osteolysis, spontaneous pain (paw licking) and evoked pain (mechanical and col allodynia) occur 6 days after implantation and last for at least 16 days. The rats are then divided into three groups: 1) flupirtine alone; 2) flupirtine and morphine; and 3) saline. The animals are then monitored using standard behavioural tests for pain, such as the paw withdrawal threshold or paw flick latency.

Rat Tibia Bone Cancer Model (TBC)

MRMT-1 rat mammary gland carcinoma cells are injected into the tibia bone of Sprague-Dawley rats. Bone destruction is detected within 10 days of tumor cell injection. The onset of allodynia and mechanical hyperalgesia are dose (tumor cell number)-dependent, and occur within 10-12 days of tumor cell injection. The rats are then divided into three groups: 1) flupirtine alone; 2) flupirtine and morphine; and 3) saline. The animals are then monitored using standard behavioural tests for pain, such as the paw withdrawal threshold or paw flick latency.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of said steps or features.

BIBLIOGRAPHY

Amer et al., Pain, 33:11-23, 1988
Avidan et al., Israel Journal of Medical Sciences, 32:331-334, 1996
Bundgaard, H., Design of Prodrugs, Elsevier: 1985
Courteix et al., Pain, 53:81-88, 1993
Daut et al., Pain, 17:197-210, 1983
Davis et al., Pharmacology, Biochemistry and Behavior, 39:737-742, 1991
Galer, B. S., Neurology, 45: Suppl. 9 S17-S25, 1995
Galer and Jensen, Neurology, 48:332-338, 1997
Krause and Backonja. The Clinical Journal of Pain 19: 306-314 2003
Max, M. B., Pain, 42:131-133, 1990
Max, M. B., Pain, 50:3-4, 1992
Portenoy et al., Pain. 43(3):273-86, 1990
Randall and Selitto, Archiv. Inst. Pharmacdynamie, 111:409, 1957
Remmingtons Pharmaceutical Sciences 18$^{th}$ Edition, Mack Publishing Co., Easton, Pa., USA, 1990
Sindrup and Jensen, Pain; 83:389-400, 1999
Sindrup et al., Pain, 42:135-144, 1990
Woolf and Mannion Pai, 353:1959-64, 1999
Zimmerman, M., Pain, 16:109-110, 1983

The invention claimed is:

1. A method for inducing an analgesic response to neuropathic cancer pain in a mammal, said method comprising selecting the mammal with neuropathic cancer pain, and administering to the mammal, a composition comprising the structure

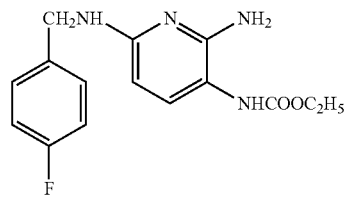

or a pharmaceutically acceptable salt thereof in combination with morphine, in an amount effective to reduce the level of or to otherwise ameliorate the sensation of neuropathic cancer pain, excluding topical administration.

2. The method of claim 1, further comprising the administration of morphine concurrently or sequentially to the flupirtine.

3. The method claim 1, wherein morphine does not induce overt sedation in the presence of flupirtine.

4. The method of claim 1, wherein flupirtine is administered in an amount of about 0.5 mg/kg to about 20 mg/kg of body weight.

5. The method of claim 1, wherein the mammal is human.

6. The method of claim 5, wherein the cancer is selected from the group consisting of ABL1 protooncogene, AIDS Related Cancers, Acoustic Neuroma, Acute Lymphocytic Leukaemia, Acute Myeloid Leukaemia, Adenocystic carcinoma, Adrenocortical Cancer, Agnogenic myeloid metaplasia, Alveolar soft-part sarcoma, Anal cancer, Angiosarcoma, Aplastic Anaemia, Astrocytoma, Basal Cell Carcinoma (Skin), Bladder Cancer, Bone Cancers, Bowel cancer, Brain Stem Glioma, Brain and CNS Tumors, Breast Cancer, CNS tumors, Carcinoid Tumors, Cervical Cancer, Childhood Brain Tumors, Childhood Cancer, Childhood Leukaemia, Childhood Soft Tissue Sarcoma, Chondrosarcoma, Choriocarcinoma, Chronic Lymphocytic Leukaemia, Chronic Myeloid Leukaemia, Colorectal Cancers, Cutaneous T-Cell Lymphoma, Dermatofibrosarcoma-protuberans, Desmoplastic-Small-Round-Cell-Tumor, Ductal Carcinoma, Endocrine Cancers, Endometrial Cancer, Ependymoma, Esophageal Cancer, Ewing's Sarcoma, Extra-Hepatic Bile Duct Cancer, Eye Cancer, Eye: Melanoma, Retinoblastoma, Fallopian Tube cancer, Fibrosarcoma, Gall Bladder Cancer, Gastric Cancer, Gastrointestinal Cancers, Gastrointestinal-Carcinoid-Tumor, Genitourinary Cancers, Germ Cell Tumors, Gestational-Trophoblastic-Disease, Glioma, Gynaecological Cancers, Haematological Malignancies, Hairy Cell Leukaemia, Head and Neck Cancer, Hepatocellular Cancer, Hereditary Breast Cancer, Histiocytosis, Hodgkin's Disease, Hypopharynx Cancer, IntraOcular Melanoma, Islet cell cancer, Kaposi's sarcoma, Kidney Cancer, Langerhan's-Cell-Histiocytosis, Laryngeal Cancer, Leiomyosarcoma, Leukaemia, Li-Fraumeni Syndrome, Lip Cancer, Liposarcoma, Liver Cancer, Lung Cancer, Lymphoma, Hodgkin's Lymphoma, Non-Hodgkin's Lymphoma, Male Breast Cancer, Malignant-Rhabdoid-Tumor-of-Kidney, Medulloblastoma, Melanoma, Merkel Cell Cancer, Mesothelioma, Metastatic Cancer, Mouth Cancer, Multiple Endocrine Neoplasia, Myelodysplastic Syndromes, Myeloma, Myeloproliferative Disorders, Nasal Cancer, Nasopharyngeal Cancer, Nephroblastoma, Neuroblastoma, Neurofibromatosis, Non-Melanoma Skin Cancer, Non-Small-Cell-Lung-Cancer-(NSCLC), Ocular Cancers, Oesophageal Cancer, Oral cavity Cancer, Oropharynx Cancer, Osteosarcoma, Ostomy Ovarian Cancer, Pancreas Cancer, Paranasal Cancer, Parathyroid Cancer, Parotid Gland Cancer, Penile Cancer, Peripheral-Neuroectodermal-Tumors, Pituitary Cancer, Prostate Cancer, Rare-cancers-and-associated-disorders, Renal Cell Carcinoma, Retinoblastoma, Rhabdomyosarcoma, Salivary Gland Cancer, Sarcoma, Schwannoma, Sezary syndrome, Skin Cancer, Small Cell Lung Cancer (SCLC), Small Intestine Cancer, Soft Tissue Sarcoma, Spinal Cord Tumors, Squamous-Cell-Carcinoma-(skin), Stomach Cancer, Synovial sarcoma, Testicular Cancer, Thymus Cancer, Thyroid Cancer, Transitional-Cell-Cancer-(bladder), Transitional-Cell-Cancer (renal-pelvis-/-ureter), Trophoblastic Cancer, Urethral Cancer, Urinary System Cancer, Uterine sarcoma, Uterus Cancer, Vaginal Cancer, Vulva Cancer, Waldenstrom's-Macroglobulinemia, and Wilms' Tumor.

* * * * *